US011518991B2

(12) United States Patent
Zeisberg et al.

(10) Patent No.: US 11,518,991 B2
(45) Date of Patent: Dec. 6, 2022

(54) METHOD FOR RE-EXPRESSION OF DIFFERENT HYPERMETHYLATED GENES INVOLVED IN FIBROSIS, LIKE HYPERMETHYLATED RASAL1 AND USE THEREOF IN TREATMENT OF FIBROSIS AS WELL AS KIT OF PARTS FOR RE-EXPRESSION OF HYPERMETHYLATED GENES INCLUDING RASAL1 IN A SUBJECT

(71) Applicant: GEORG-AUGUST-UNIVERSITÄT GÖTTINGEN STIFTUNG ÖFFENTLICHEN RECHTS, UNIVERSITÄTSMEDIZIN, Göttingen (DE)

(72) Inventors: Elisabeth Zeisberg, Göttingen (DE); Xingbo Xu, Göttingen (DE)

(73) Assignee: Georg-August-Universitaet Goettingen Stiftung Oeffentlichen Rechts, Universitaetsmedizin, Goettingen (DE)

( * ) Notice: Subject to any disclaimer, the term of this patent is extended or adjusted under 35 U.S.C. 154(b) by 293 days.

(21) Appl. No.: 16/488,131

(22) PCT Filed: Feb. 26, 2018

(86) PCT No.: PCT/EP2018/054619
§ 371 (c)(1),
(2) Date: Aug. 22, 2019

(87) PCT Pub. No.: WO2018/154096
PCT Pub. Date: Aug. 30, 2018

(65) Prior Publication Data
US 2019/0382752 A1    Dec. 19, 2019

(30) Foreign Application Priority Data
Feb. 24, 2017 (EP) .................... 17157906

(51) Int. Cl.
| | |
|---|---|
| *C12N 15/10* | (2006.01) |
| *C12N 15/113* | (2010.01) |
| *C12N 9/02* | (2006.01) |
| *C12N 9/22* | (2006.01) |
| *C12N 15/67* | (2006.01) |

(52) U.S. Cl.
CPC ......... *C12N 15/102* (2013.01); *C12N 9/0071* (2013.01); *C12N 9/22* (2013.01); *C12N 15/113* (2013.01); *C12N 15/67* (2013.01); *C12N 2310/20* (2017.05)

(58) Field of Classification Search
None
See application file for complete search history.

(56) References Cited

U.S. PATENT DOCUMENTS

| | | |
|---|---|---|
| 9,512,446 B1 | 12/2016 | Joung et al. |
| 2016/0010076 A1 | 1/2016 | Joung et al. |
| 2021/0171944 A1* | 6/2021 | Chen ................. C12N 15/67 |

FOREIGN PATENT DOCUMENTS

| | | |
|---|---|---|
| WO | 2017/208247 A1 | 12/2017 |
| WO | 2018/035495 A1 | 2/2018 |

OTHER PUBLICATIONS

Xu et al.; "A CRISPR-based approach for targeted DNA demethylation"; Cell Discovery, vol. 2, No. 1, May 3, 2016, pp. 1-12.
Choudhury et al.; "CRISPR-dCas9 mediated TET1 targeting for selective DNA demethylation at BRCA1 promoter"; Oncotarget, vol. 7, No. 29, Jun. 23, 2016, pp. 46545-46556.
Tampe et al.; "Tet3-Mediated Hydroxymethylation of Epigenetically Silenced Genes Contributes to Bone Morphogenic Protein 7-Induced Reversal of Kidney Fibrosis"; Journal of the American Society of Nephrology, vol. 25, No. 5, Jan. 30, 2014, pp. 905-912.
Tampe et al.; "Low-dose hydralazine prevents fibrosis in a murine model of acute kidney injury-to-chronic kidney disease progression"; Kidney International, vol. 91, No. 1, Sep. 28, 2016, pp. 157-176.
Geurs; "Ontwikkelen van kankermodellen in Xenopus via TALEN-en CRISPR/Cas-gemedieerde genoom-modificatie"; M. Sc. theses, 2015, pp. i-iv, 1-50, a-k.
Chamberlain et al.; "Expressing Transgenes That Exceed the Packaging Capacity of Adeno-Associated Virus Capsids"; Human Gene Therapy Methods, vol. 27, No. 1, Jan. 11, 2016, pp. 1-12.
Xu et al.; "Epigenetic balance of aberrant Rasal1 promoter methylation and hydroxymethylation regulates cardiac fibrosis"; Cardiovascular Research, vol. 105, No. 3, Jan. 23, 2015, pp. 279-291.
Liu et al.; "Editing DNA Methylation in the Mammalian Genome"; Cell, vol. 167, No. 1, Sep. 22, 2016, pp. 233-247.
Morita et al.; "Targeted DNA demethylation in vivo using dCas9-peptide repeat and scFv-TET1 catalytic domain fusions"; Nature Biotechnology, vol. 34, No. 10, Aug. 29, 2016, pp. 1060-1065.
Qiao et al.; "Enforced expression of RASAL1 suppresses cell proliferation and the transformation ability of gastric cancer cells"; Oncology Reports, vol. 28, No. 4, Jul. 19, 2012, pp. 1475-1481.

(Continued)

*Primary Examiner* — Brian Whiteman
(74) *Attorney, Agent, or Firm* — WCF IP

(57) ABSTRACT

A method for re-expression of hypermethylated RASAL1, hypermethylated LRFN2, and hypermethylated KLOTHO based on an inactivated CRISPR-based system and a DNA dioxygenase as well as a gRNA guiding the construct to the RASAL1, LRFN2, and KLOTHO gene for demethylation of hypermethylated RASAL1, hypermethylated LRFN2, and hypermethylated KLOTHO, in particular, hypermethylated RASAL1, LRFN2, and KLOTHO promoter, thus, allowing re-expression of RASAL1, LRFN2, and KLOTHO for the treatment of fibrosis, cancer or neuronal disorders in a subject is provided. A kit of parts for allowing re-expression of hypermethylated RASAL1, hypermethylated LRFN2, and hypermethylated KLOTHO in a subject, a vector or vector system, and nucleic acid constructs are also provided.

Figure 1A:
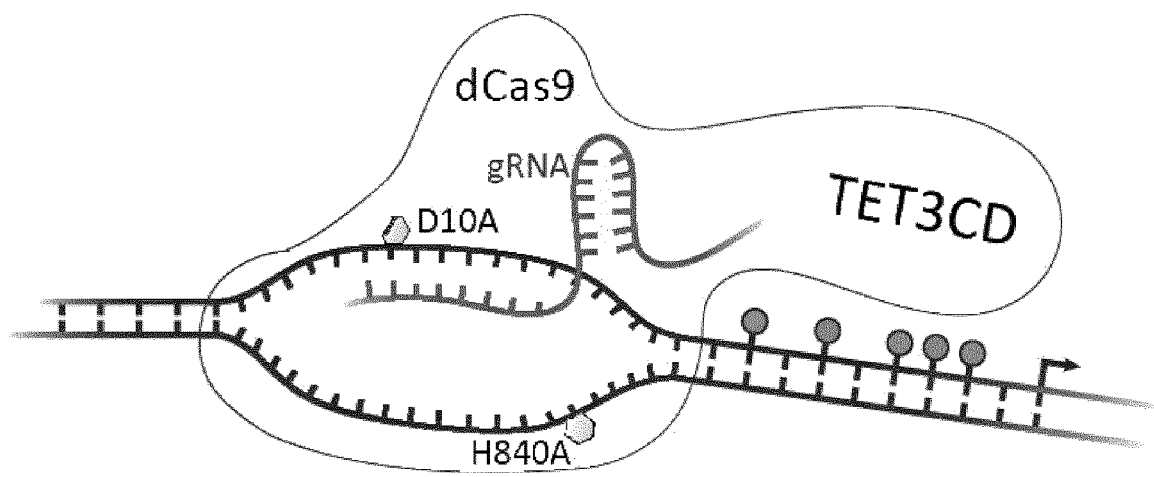
Figure 1B:
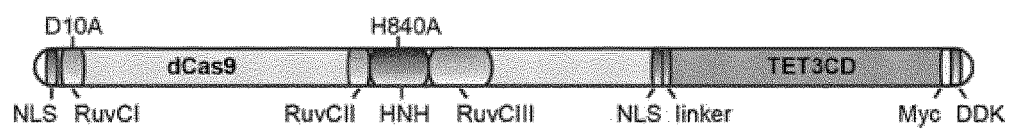

13 Claims, 7 Drawing Sheets
Specification includes a Sequence Listing.

(56) References Cited

OTHER PUBLICATIONS

Tampe et al.; "Induction of Tet3-dependent Epigenetic Remodeling by Low-dose Hydralizine Attenuates Progression of Chronic Kidney Disease"; EBIOMEDICINE, vol. 2, No. 1, Nov. 8, 2014, pp. 19-36.
Jin et al., "TET1 is a maintenance DNA demethylase that prevents methylation spreading in differentiated cells", Nucleic Acids Research, 2014.
Choudhury et al., "CRISPR-dCas9 mediated TET1 targeting for selective DNA demethylation at BRCA1 promoter", Oncotarget, vol. 7, No. 29, 2016.
Zetsche et al., "Cpf1 is a single RNA-guided endonuclease of a Class 2 CRISPR-Cas system", Cell, Oct. 22, 2015; 163(3): 759-771.
Tampe et al.,"Tet3-Mediated Hydroxymethylation of Epigenetically Silenced Genes Contributes to Bone Morphogenic Protein 7-Induced Reversal of Kidney Fibrosis", J Am Soc Nephrol 25: 905-912, 2014.
Xu et al., "Epigenetic balance of aberrant Rasal1 promoter methylation and hydroxymethylation regulates cardiac fibrosis", Cardiovascular Research (2015) 105, 279-291.
Xu et al., "A CRISPR-based approach for targeted DNA demethylation", Cell Discovery (2016) 2, 16009.

\* cited by examiner

METHOD FOR RE-EXPRESSION OF DIFFERENT HYPERMETHYLATED GENES INVOLVED IN FIBROSIS, LIKE HYPERMETHYLATED RASAL1 AND USE THEREOF IN TREATMENT OF FIBROSIS AS WELL AS KIT OF PARTS FOR RE-EXPRESSION OF HYPERMETHYLATED GENES INCLUDING RASAL1 IN A SUBJECT

The present invention relates to a method for re-expression of hypermethylated RASAL1, hypermethylated LRFN2, and hypermethylated KLOTHO based on an inactivated CRISPR-based system and a DNA dioxygenase as well as a gRNA guiding said construct to the RASAL1, LRFN2, and KLOTHO gene, respectively, for demethylation of at least one of hypermethylated RASAL1, hypermethylated LRFN2, and hypermethylated KLOTHO, in particular, hypermethylated RASAL1, LRFN2, and KLOTHO promoter, thus, allowing re-expression of at least one of RASAL1, hypermethylated LRFN2, and hypermethylated KLOTHO for the treatment of fibrosis, cancer or neuronal disorders in a subject. Further, the present invention relates to a kit of parts for allowing re-expression of at least one of hypermethylated RASAL1, hypermethylated LRFN2, and hypermethylated KLOTHO in a subject comprising nucleic acid encoding the gRNA as defined above as well as a fusion protein of an inactive CRISPR based system and a DNA dioxygenase. Finally, the present invention provides a vector or vector system composed of at least two vectors, the vector or vector system comprises the nucleic acids encoding the gRNA as well as the fusion protein in a single vector or in two vectors. Further, nucleic acid constructs are provided comprising the nucleic acid encoding the gRNA as well as the fusion protein.

PRIOR ART

Aberrant CpG island promoter methylation of select genes contributes causally to various pathologies. One example is RASAL1, which encodes for a Ras-GAP-like Ras-GTP inhibitor, and hypermethylation of the RASAL1 promoter leads to silencing of RASAL1 expression and increased RAS-GTP activity. The RASAL1 promoter is consistently hypermethylated in tissue fibrosis including kidney, heart and liver and also in gastrointestinal cancers. The extent of RASAL1 promoter methylation correlates with progression of kidney fibrosis in patients and mice, and rescue of RASAL1 transcription through transgenic overexpression attenuates progression of experimental fibrosis in the kidney (Tampe, B. et al. *E Bio Medicine* 2, 19-36 (2015)), revealing reversal of aberrant RASAL1 methylation and rescue of RASAL1 expression as therapeutic targets to inhibit progression of kidney fibrosis.

RASAL1 was originally identified as one of 2 genes (LRFN2, encoding for leucine-rich repeat and fibronectin type III domain-containing protein, which functions in presynaptic differentiation) in a genome-wide methylation screen comparing normal and fibrotic kidney fibroblasts, which were consistently downregulated and hypermethylated in fibrotic but not healthy fibroblasts both in humans and mouse.

Hypermethylation of the KLOTHO promoter has been shown to be associated with progression of various forms of cancer and to correlate with kidney fibrosis in both humans and experimental fibrosis mouse models. In the kidney, Klotho is predominantly expressed in tubular epithelial cells. Reversal of hypermethylated Klotho promoter associated Klotho suppression by a lipophilic anthraquinone compound, Rhein, has been demonstrated to ameliorate renal fibrosis in UUO-induced fibrotic kidney mouse model. This results through effectively reducing aberrant DNMT1/3a expression and thereby maintaining secreted and membrane Klotho levels.

It has long been known that DNA methylation can be inhibited through administration of nucleotide analogues such as 5'azacytidine, which are incorporated into DNA and which cause DNA damage to induce DNA repair, resulting in replacement with unmethylated DNA. While nucleotide analogues are in clinical use as demethylating therapies, they are highly unspecific and their utility is limited as second line therapies in myelodysplastic syndromes due to side effects, highlighting the need for gene specific, less toxic demethylating therapies.

In this regard, members of the ten-eleven translocation (TET) family of zinc finger proteins catalyse oxidation of methylated cytosine residues (so-called hydroxymethylation), which subsequently leads to replacement of methylated cytosine residues with naked cytosine. Both hydroxymethylated and demethylated promoters result in re-expression of genes that had been silenced through CpG promoter methylation. It has been shown previously that in the kidney TET3 is the predominant TET protein, that kidney fibrosis is associated with decreased TET3 expression, and that induction of endogenous TET3 expression led to hydroxymethylation and demethylation of various genes, including RASAL1 within diseased kidneys and attenuated experimental kidney fibrosis (Tampe, B. et al. *Journal of the American Society of Nephrology* 25, 905-912 (2014); Tampe, B. et al. *E Bio Medicine* 2, 19-36 (2015)). TET3 only induces transcription of genes that had been previously methylated, and it is recruited to select genes (including RASAL1) through recognition of a common CXXC motif in proximity to gene promoter CpG islands, providing enhanced specificity as compared to nucleotide analogues. As opposed to silencing of DNMTs, activation of TET enzymes is an active way of reducing aberrant gene methylation. However, there are more than 9000 genes targeted by TET proteins within the human genome, suggesting gene-specific delivery of TET as an attractive approach to rescue expression of aberrantly methylated genes.

In this regard, previous studies demonstrated that by fusion of the TET methylcytosine dioxygenase catalytic domain (in which the CXXC binding domain is lacking) to the programmable DNA-binding domains of zinc figure proteins (ZFPs) or of transcription activator-like effector (TALE), enhanced gene-specificity of hydroxymethylation and re-expression of methylated genes could be achieved as compared to globally increased Tet expression. However, utility of these approaches was limited due to off-target effects, high labour intensity and lack of evidence for disease modifying in vivo activities, revealing that a technique with further enhanced specificity was needed.

In US 2016/0010076 A1 RNA guided targeting of genetic and epigenomic regulatory proteins to specific genomic loci are described. The document discloses a fusion protein of catalytically inactive CRISPR associated 9 (dCas9) linked to a heterologous functional domain whereby said heterologous functional domain may be an enzyme that modifies the methylation state of DNA, like the TET protein. The use of a CRISPR-based approach for targeted DNA demethylation has been described recently and will be discussed below.

Further, the intermediate document U.S. Pat. No. 9,512,446 B1 identifies engineered CRISPR/Cas9 nucleases wherein mutations are present at positions Q695 and Q926 and, in addition, further, containing mutations at N497 and R661. A high fidelity CRISPR/Cas9 variant with undetectable genome-wide off-targets is described by Kleinstiver, B. P. et al, Nature 2016, 529 (7587): 490-495; doi:10.1038/nature16526.

DESCRIPTION OF THE PRESENT INVENTION

The present invention aims to provide a method and system allowing gene-specific hydroxymethylation via a CRISPR-based system, thus, rescuing expression of at least one of methylated RASAL1, methylated LRFN2, and methylated KLOTHO in particular, useful in attenuating and treating fibrosis as well as cancer and neuronal disorders.

That is, in a first aspect, the present invention provides a method for the treatment of a disease, disorder or condition selected from fibrosis, neuronal degeneration or cancer comprising the steps of re-expression of at least one of hypermethylated RASAL1, hypermethylated LRFN2, and hypermethylated KLOTHO in cells comprising the steps of introducing in cells nucleic acid encoding a gRNA guiding a fusion protein composed of an inactive CRISPR based system and a DNA dioxygenase to one of the RASAL1, LRFN2, or KLOTHO gene, in particular, the promoter region of the RASAL1, LRFN2, or KLOTHO gene; and nucleic acid encoding a fusion protein composed of an inactive CRISPR system and a DNA dioxygenase;

demethylation of at least one of hypermethylated RASAL1, hypermethylated LRFN2, and hypermethylated KLOTHO, in particular, hypermethylated RASAL1 promoter, for re-expression of RASAL1, LRFN2, or KLOTHO in said cells.

In a further embodiment, the present invention relates to a method for re-expression of at least one of hypermethylated RASAL1, hypermethylated LRFN2, and hypermethylated KLOTHO in cells comprising the steps of introducing in cells nucleic acid encoding a gRNA guiding a fusion protein composed of an inactive CRISPR based system and a DNA dioxygenase to the RASAL1, LRFN2, or KLOTHO gene, in particular, the promoter region of the RASAL1, LRFN2, or KLOTHO gene; and nucleic acid encoding a fusion protein composed of an inactive CRISPR system and a DNA dioxygenase;

demethylation of at least one of hypermethylated RASAL1, hypermethylated LRFN2, and hypermethylated KLOTHO, in particular, hypermethylated RASAL1 promoter, for re-expression of at least one of RASAL1, LRFN2, or KLOTHO in said cells.

In an embodiment of the present invention, at least two of the hypermethylated genes of RASAL1. LRFN2 and KLOTHO are targeted, like all of the three genes. The combinations are RASAL1 and LRFN2, RASAL1 and KLOTHO, and LRFN2 and KLOTHO as well as all of them.

The present inventors recognized that based on the method provided, it is possible to re-express the RASAL1 gene product, the LRFN2 gene product, and/or the KLOTHO gene product, thus, demonstrating beneficial effects on fibrosis, cancer and neuronal disorders, in particular, fibrosis.

The present inventors aim the first gene-specific demethylating treatment in a disease model in vivo having potential as precision medicine for disease caused by aberrant promoter methylation. That is, with the present invention it is possible to reverse hypermethylation of predetermined gene(s), in particular, at least one of RASAL1, LRFN2, or KLOTHO.

The method according to the present invention is thus particularly useful for use in the treatment of gene hypermethylation, like promoter hypermethylation, caused diseases such as fibrosis, neuronal disorders as well as cancer. The fibrosis include any one of the fibrosis known in the art, in particular, kidney fibrosis, liver fibrosis, heart fibrosis, lung fibrosis as well as cancer including gastrointestinal cancers, breast cancer, hodgkin lymphoma, adenocarcinoma, colon cancer, thyroid cancer, liver cancer, gastric cancer and colorectal cancer, or glaucoma.

In an embodiment of the present invention, the DNA dioxygenase is selected from the TET protein family. For example, the TET protein is any one of TET1, TET2 or TET3. In an embodiment, the TET3 catalytic domain (TET3CD) is used. In another embodiment, e.g. in case of an AAV based vector, the TET protein is the TET1 catalytic domain (TET1CD).

In an embodiment suitable for the treatment of the disease identified above including fibrosis or gastrointestinal cancer, the DNA dioxygenase is the TET3 catalytic domain. In another embodiment thereof, the DNA dioxygenase is the TET1CD.

Further, an embodiment of the method according to the present invention is a method wherein the hypermethylated region of at least one of the RASAL1, LRFN2, or KLOTHO gene is the promoter region and the gRNA is a gRNA guiding the fusion protein composed of the inactive CRISPR-based system and the DNA methyltransferase to the promoter region of at least one of RASAL1, LRFN2, or KLOTHO, thus, demethylating the same.

In an embodiment the CRISPR system is a class I or class II system. Class II CRISPR systems use a single Cas protein with the respective RNA molecule while class I systems require a complex of multiple proteins to degrade for nucleic acids, the class II systems use a single large Cas protein for the same purpose. The main representative of the CRISPR based system is the CRISPR Cas system and the CRISPR CPF system. In an embodiment of the present invention, the CRISPR system is the Cas system, in particular, the Cas9 system. The Cas9 system may be from *S. pyogenes, S. aureus*, etc. as known in the art. The CPF system, in particular the Cpf1 system, may be from *S. thermophilus*, etc. In an embodiment, the CRISPR system is based on a mutated Cas9 system, also called dCas9 or, a mutated Cpf1 system. In an embodiment, the dCas9 has the mutations D10A and H840A, e.g. as described in US20160010076A1. In an embodiment, a deactivated high fidelity Cas9 is described containing beside the referenced mutations and positions D10A and H840A further mutations, namely, at positions Y450A, N497A, R661A, Q695A and Q926A. The specific deactivated Cas, in the following abbreviated with dhfCas9, is particularly useful according to the present invention that is, in a particular embodiment, the dCas9 is the described dhfCas9 with the mutations identified.

That is, a method according to the present invention is a method wherein at least one of the hypermethylated RASAL1, LRFN2, or KLOTHOgene region is the promoter region of the RASAL1, LRFN2, or KLOTHOgene, the inactive CRISPR system is the inactive Cas9 having the mutations D10A and H840A and the DNA methyltransferase is the TET3 catalytic domain.

In addition, in an embodiment the method is a method wherein the hypermethylated RASAL1, LRFN2, or KLOTHO gene region is the promoter region of the RASAL1, LRFN2, or KLOTHO gene, the inactive CRISPR system is the inactive Cas9 having the mutations D10A, Y450A, N497A, R661A, Q695A, H840A and Q926A and the DNA methyltransferase is the TET3 catalytic domain.

Embodiments of suitable nucleic acids are given as follows:

Suitable gRNA sequences are the sequences of SEQ ID Nos. 3 to 7 an 16 (human) and 8 to 13 (mouse). Further sequences are for the LRFN2 gRNA the sequences of SEQ ID. Nos. 17 an 18, for the human KLOTHO gene sequences of SEQ ID. Nos 19 an 20 and for the mouse KLOTHO gene sequences of SEQ ID. Nos. 21, 22, and 23.

The human RASAL1 promoter region is given in SEQ ID No. 1, the mouse RASAL1 promoter region is given in SEQ ID No. 2.

The complete amino acid sequence of dCas9-TET3CD fusion protein is given in SEQ ID No. 15. In SEQ ID. No. 15, the complete amino acid sequence of the dHFCas9-TET3CD is shown.

According to the method of the present invention, introduction of the nucleic acid may be effected by known means. For example, the nucleic acids may be introduced as an all-in-one construct, that is, a single vector comprising all nucleic acids as defined in the method according to the present invention, or as a nucleic acid construct as defined herein. Alternatively, the introduction of the nucleic acids may be effected with two or more vector systems. However, it is possible to introduce the same by a single vector, thus, increasing the efficiency of successful introduction.

The introduction may be effected by known vector systems or other methods for introducing nucleic acids in cells. For example, known transfection systems including liposomes etc. may be used.

When introducing the nucleic acid according to the present invention in cells wherein the RASAL1, LRFN2, and KLOTHO gene is not hypermethylated, in particular, wherein the promoter region of the RASAL1, LRFN2, and KLOTHO gene is not hypermethylated, no adverse effects can be observed.

In a further aspect, the present invention relates to a kit of parts for allowing the re-expression of at least one of hypermethylated RASAL1, hypermethylated LRFN2, and hypermethylated KLOTHO in cells of a subject comprising a nucleic acid encoding a gRNA guiding a fusion protein of an inactive CRISPR based system and a DNA dioxygenase to the RASAL1, LRFN2, or KLOTHO gene, in particular, the promoter region of RASAL1, LRFN2, or KLOTHO; a nucleic acid encoding a fusion protein composed of an inactive CRISPR system and a DNA dioxygenase, and optionally, means for introducing said nucleic acids into a cell.

In the kits of part according to the present invention, the nucleic acids may be present as a single nucleic acid construct, e.g. in form of a vector or may be present in more than one component, e.g. in two vectors or more than two vectors. It is envisaged to provide the nucleic acids as a single construct. The kit of parts may optionally contain other means for allowing introduction of the nucleic acids into the cells. These other means include the suitable vector or vector systems, e.g. lentivirus, AAV virus (adeno-associated virus), adenovirus, retrovirus, etc. Other systems may be based on known transfection systems based on liposomes etc.

That is, in the method according to the present invention all the kits of part according to the present invention, a suitable vector or vector system is a lentivirus based vector or an AAV based vector or corresponding vector system. A skilled person is well aware of suitable systems working in the subject to be treated or the cells to be infected.

In an embodiment of the kit of part according to the present invention, the gRNA guiding the fusion protein composed of an inactive CRISPR based system and a DNA dioxygenase is a gRNA guiding the fusion protein composed of an inactive CRISPR system and a DNA dioxygenase to the hypermethylated promoter region of the RASAL1, LRFN2, and KLOTHO and/or the inactive CRISPR system is a mutated Cas9 and/or a mutated Cfp1, in particular, a mutated dCas9 having the mutations D10A and H840A and/or the DNA methyltransferase is the TET3CD or the TET1CD.

In an embodiment of the present invention, the kit of parts according to the present invention the gRNA guiding the fusion protein composed of an inactive CRISPR based system and a DNA dioxygenase is a gRNA guiding the fusion protein composed of an inactive CRISPR system and a DNA dioxygenase to the hypermethylated promoter region of the RASAL1, LRFN2, KLOTHO and/or the inactive CRISPR system is a mutated Cas9, namely, the dhfCas9 having the mutations D10A, Y450A, N497A, R661A, Q695A, H840A and Q926A and/or the DNA methyltransferase is the TET3CD or the TET1CD.

In another embodiment of the kit of part, the nucleic acids being present in a vector system comprising two separate vectors wherein one vector contains the nucleic acid encoding the gRNA and the other vector contains the nucleic acid encoding the fusion protein composed of the inactivated CRISPR system and the DNA dioxygenase.

In another aspect, the present invention provides i) a vector or ii) a vector system composed of at least two vectors, said vector or vector system comprising the nucleic acids encoding the gRNA guiding a fusion protein composed of an inactivated CRISPR system and a DNA dioxygenase to at least one of the RASAL1, LRFN2, and KLOTHO gene, in particular, to the promoter of at least one of the RASAL1, LRFN2, and KLOTHO gene, and nucleic acid encoding a fusion protein composed of an inactivated CRISPR system and DNA methyltransferase, in particular, as defined herein.

In another aspect, the kit of part according to the present invention or the vector or vector system according to the present invention is for use in the treatment of DNA methylation caused diseases such as neuronal degeneration, fibrosis or cancer.

In another aspect, the present invention provides a nucleic acid construct comprising a nucleic acid encoding a gRNA guiding a fusion protein composed of an inactivated CRISPR system and a DNA dioxygenase to at least one of the RASAL1, LRFN2, and KLOTHO gene, in particular, the promoter region of at least one of RASAL1, LRFN2, and KLOTHO gene, and nucleic acid encoding a fusion protein composed of an inactivated CRISPR system and a DNA dioxygenase.

In an embodiment of said nucleic acid construct, the nucleic acid construct is a construct wherein the gRNA is a gRNA guiding the fusion protein encoding the inactivated CRISPR system and the DNA dioxygenase to at least one of the hypermethylated promoter region of RASAL1, LRFN2, and KLOTHO, the nucleic acid encoding the fusion protein composed of an inactivated CRISPR system and a DNA dioxygenase is a nucleic acid encoding a mutated dCas9 having mutations at D10A and H810A and the TET3CD. Alternatively, the system of dCas having mutations at D10A and H810A and the TET1CD construct is used. Further instead of using a mutated dCas9 a mutated Cpf1 may be used. In a further embodiment, the system of the dCas is a dhfCas9 as described. That is, in a further embodiment, the present invention relates to a gRNA molecule guiding a fusion protein composed of the inactivated CRISPR system and a DNA dioxygenase to at least one of the RASAL1 gene, LRFN2 gene, or KLOTHO gene, in particular, the promoter region of said genes, like the promoter region of the RASAL1 gene.

Moreover, the present invention relates to a nucleic acid construct comprising a nucleic acid encoding a mutated dCas9, namely, encoding the dhfCas9 as described herein having mutations at D10A, Y450A, N497A, R661A, Q695A, H810A, and Q926A. In an embodiment, the nucleic acid construct according to the present invention is a nucleic acid construct comprising the dhfCas9 in combination with the DNA dioxygenase described herein, like the TET3CD or the TET1CD and, alternatively, or in combination, with any one of the genes of DMT3A, LSD1, P300, CAP1, VP64.

The skilled person is well aware of obtaining a nucleic acid construct according to the present invention by known means.

Further, the method for treating fibrosis, neuronal disorders or cancer as described herein may be effected by known means. For example, administration may be effected systemically or locally.

Finally, the present invention provides a vector or vector system. This system is an AAV system containing the nucleic acids encoding the gRNA as defined herein, namely, the gRNA guiding a fusion protein composed of an inactivated CRISPR system and a dioxygenase system to the RASAL1, LRFN2, or KLOTHO gene. The vector or vector system may be a vector system known as overloaded AAV system, an AAV having splitted nucleic acid constructs or a normal AAV system.

The skilled person is well aware of suitable methods with respect to the referenced vector systems. For example, suitable systems are described in Trapani, et al., EMBO Mol Med 2014, 6:194-211 for splitting, and for overloaded or designed systems in Dong, et al., Mol Ther 2010, 18:87-92, Deverman, et al., Nat Biotechnol 2016, 34:204-209; Landegger, et. A I., Nat Biotechnol 2017, 35:280-284, as well as WO2016164609, and WO2005033321.

In the following, the present invention will be described further by way of examples without limiting the same.

Material and Methods

Plasmids

The RASAL1/Rasal1 sgRNA sequences as well as the sgRNA sequences of LRFN2 and KLOTHO were designed and were off-target predicted by the online tool Blueheronbio (Origene, Herford, Germany). The control LacZ sgRNA sequence was the same as previously reported (Platt, R. J. et al. Cell 159, 440-455 (2014). The sequences were inserted into the pLenti-Cas-Guide plasmid (Origene, Herford, Germany) with BamHI and BsmBI restriction sites to generate pLenti-Cas-RASAL1/Rasal1/LacZ as well as the corresponding LRFN2 and KLOTHO constructs and confirmed by DNA sequencing. In the following the process is described for RASAL only. The gene targeting properties for each construct were assessed by cleavage assay. The wild-type Cas9 open reading frame was removed from the vector with Age1 and Not1 sites. The plasmid encoding H840A Cas9 was obtained from Addgene (#39316). The pLenti-dCas9 (deactivated endonuclease activity Cas9)-RASAL1/Rasal1/LacZ constructs were generated by cloning dCas9 into the cut pLenti-Cas-RASAL1/Rasal1/LacZ vectors in frame by PCR using Phusion high-fidelity DNA polymerase (NEB, Ipswich, USA) with Age1 (5') and Xba1, Not1 (3') restriction sites with two NLS (nuclear localization signal) peptides at the N and C-terminus each with a primer pair that introduced the D10A mutation. The TET3 CD (catalytic domain, a.a 850-1795) was amplified from a human TET3 ORF (Origene, Herford, Germany) with a primer pair which introduced Age1, a start codon, Xba1, a Gly-Gly-Gly-Ser-Gly (SEQ ID No. 14) linker (5') and Not1 (3') restriction sites and then inserted into the cut pLenti-Cas-LacZ vector to generate pLenti-TET3CD-LacZ. The sequence and the coding frame for dCas9 and for TET3 CD were confirmed by DNA sequencing and by Western Blot. The final constructs pLenti-dCas9-TET3CD-RASAL1/Rasal1/LacZ were generated by removing TET3 CD from pLenti-TET3CD-LacZ, subsequently inserted into pLenti-dCas9-RASAL1/Rasal1/LacZ with Xba1 and Not1 restriction sites. Similar constructs have been obtained for LRFN2 and KLOTHO.

DNA Isolation, MeDIP and hMeDIP Assay

Animal tissues or cell pellets were lysed by DNA lysis buffer (Qiagen, Hilden, Germany) and precipitated and purified using DNeasy Blood & Tissue Kit (Qiagen, Hilden, Germany) according to the manufacturer's protocol. Prior to immunoprecipitation, genomic DNA was sonicated (Qsonica, Newtown, USA) to produce DNA fragments ranging in size from 200 to 1000 bp, with a mean fragment size of around 300 bp. Methylated DNA was captured using Methylamp Methylated DNA Capture Kit (Epigentek, Farmingdale, USA). In total 1.0 µg of fragmented DNA was applied in every antibody-coated well and incubated at room temperature on a horizontal shaker for 2 hours. The immunoprecipitated DNA was released by proteinase K. The DNA was eluted from the column and adjusted to a final volume of 100 µl with nuclease-free water. For each sample, an input vial was included using total sonicated DNA as loading control. Hydroxymethylated DNA was captured using EpiQuick Hydroxymethylated Immunoprecipitation (hMeDIP) Kit (Epigentek, Farmingdale, USA) according to the manufacturer's protocol. 0.5 µg of sonicated DNA was added to each antibody coated well and incubated at room temperature on a horizontal shaker for 90 minutes. The DNA was released by proteinase K digestion and heat denaturized. The purified DNA was eluted and diluted to a final volume of 200 µl with nuclease-free water. For each sample, an input vial was included using total sonicated DNA as loading control.

Glucosylation-Mediated Restriction Enzyme Sensitive PCR (gRES-PCR)

The EpiMark Kit (NEB, Ipswich, USA) was used to validate the conversion from 5'mC to 5'hmC at the selected RASAL1 promoter region. The assay was performed according to the manufacturer's protocol. Briefly, 10 µg of genomic DNA was used and equally divided into two reactions, one treated with T4-phage βGT at 37° C. for 12 h, the other one was kept as untreated control. Both the βGT treated and untreated samples were then divided into three PCR tubes and digested with either MspI, HpaII or left uncut at 37° C. for a further 12 h. Samples were proteinase K treated at 40° C. for 10 min prior to dilution to 100 µl final volume in $H_2O$ and heating to 95° C. for 5 min. PCR was carried out in a volume of 5 µl for each sample on a PCR cycler (Eppendorf, Hamburg, Germany) with a standard PCR program. To visualize the PCR products, samples were loaded into the Bioanalyzer 2100 electrophoresis system (Agilent Technologies, California, USA). Electrophoresis results are shown as a virtual gel.

Bisulfite Sequencing

Purified cellular DNA was bisulfite-treated using the EZ DNA Methylation-Lightning Kit (Zymoresearch, Irvine, USA) according to the manufacture's protocol. To amplify the Rasal1 promoter fragments or the corresponding fragments of LRFN2 and KLOTHO, a touch down PCR program was performed using Taq DNA Polymerase (Sigma-Aldrich, St. Louis, USA). The first round of PCR consisted of the following cycling conditions: 94° C. for 2 min, 6 cycles consisting of 30 s at 94° C., 30 s at 60-55° C. (reduce 1° C. after each cycle) and 30 s at 72° C. The second round of PCR consisted of the following cycling conditions: 32 cycles consisting of 30 s at 94° C., 30 s at 55° C., 30 s at 72° C. The final elongation consisting of 72° C. for 6 min. The PCR products were purified using the QIAEX II Gel Extraction Kit (Qiagen, Hilden, Germany), cloned into the pGEM-T Vector (Promega, Wisconsin, United States) and transformed into Top10 Competent E. coli Cells (Life Technologies, Carlsbad, USA). The plasmid DNA was then purified with DNA Plasmid Miniprep Kit (Qiagen, Hilden, Germany) and sequenced (Seqlab, Göttingen, Germany).

Cell Culture, Transfection and Cleavage Assay

Human TK173, TK188, HEK293, 293T and mouse primary kidney fibroblast cells (passages between 3 to 5) were cultured in DMEM (Gibco, Carlsbad, USA) supplemented with 2 mmol/l L-glutamine, 100 g/ml penicillin, 100 g/ml streptomycin and 10% heat-inactivated fetal bovine serum (FBS, Cellgro, Manassas, USA) at 37° C. in 5% CO2. For transfection experiments, cells were pre-plated and cultured overnight and transfected with Lipofectamine 2000 (Life Technologies, Carlsbad, USA) according to the manufacturer's protocol. Briefly, the plasmid DNA (2.5 µg each) and Lipofectamine 2000 were mixed in a ratio of 1:2 in a total volume of 500 µl of Opti-MEM (Life Technologies, Carlsbad, USA) and incubated at room temperature to form the complex for 20 min. Then, the transfection complex was added to the cells in basic medium without serum. After overnight incubation, the medium was replaced back to complete growth medium. The cleavage assay was performed with GeneArt Genomic Cleavage Detection Kit (Life Technologies, Carlsbad, USA) according to the manufacturer's protocol. Briefly, 20 µl of cell lysis buffer and 0.8 µl of protein degrader were added to the cell pellets. After an initial program in a thermal cycler (68° C. for 15 min and 95° C. for 10 min), genomic PCR was carried out using 1-2 µl of cell lysates. The PCR products were subjected to re-annealing and a cleavage 420 assay according to the manufacturer's protocol. The products were then analyzed by the Bioanalyzer 2100 electrophoresis system (Agilent Technologies, California, USA)

Virus Packaging and Titer

Lentiviruses were produced in 293T virus packaging cells after transfection with a combination of 2nd Generation Packaging System Mix (Abmgood, Richmond, Canada), pLenti-dCas9-TET3CD-RASAL1/Rasal1/LacZ or the corresponding plasmid for LRFN2 and KLOTHO and Lentifectin (Abmgood, Richmond, Canada) according to the manufacture's protocol. Lentiviral supernatant was collected at day 2 and 3 after transfection, filtered through a 0.45 µm filter and concentrated with ultracentrifugation at 28,000 g at 4° C. using a 4% sucrose/PBS cushion for 3 hours. After centrifugation, the supernatant was removed and the viral particles were resuspended in PBS and stored at −80° C. Lentivirus titration was determined by the Lenti-X qRT-PCR Titration Kit (Clonetech, Heidelberg, Germany) and 8 µg/ml Polybrene (Sigma-Aldrich, Munchen, Germany) was used in the viral solution for the in vivo and in vitro virus transduction.

Unilateral Ureteral Obstruction (UUO) and Intrarenal Artery Infusion

All animal experiments were conducted according to the animal experimental protocols which were approved by the Institutional Review Board of the University of Göttingen and the responsible government authority of Lower Saxony (Germany). 8 to 12 week old wild type C57BL/6N mice were used for the study. After anesthesia with isoflurane inhalation, analgesia was performed by subcutaneous Buprenorphine injection. The ureter was separated from the surrounding tissues and the left ureter was clamped distal to the infusion site by two ligatures. Subsequently, the ureteropelvic junction was cannulated with a 30-gauge needle. Viral solution containing $1\times10^8$ TUs of dCas9-TET3CD-Rasal1/LacZ or the corresponding TUs of the KLOTHO plasmid in 80 µl volume was slowly injected under gentle pressure to avoid leaking of the injection solution, the abdominal muscles were sutured with absorbable suture, and the skin was closed with non-absorbable suture. Mice were sacrificed 10 days after ureter ligation and viral solution injection, the UUO and the contralateral kidney were removed for histological analysis.

Histology and Immunofluorescence

Paraffin-embedded kidneys were sectioned at 3 µm and Masson's Trichrome Stain (MTS) was performed at the University Medical Center Göttingen. We assessed the fibrotic area using CellSens (Olympus, Tokyo, Japan) software, as previously described. For immunofluorescent staining, primary antibodies against α-smooth muscle actin (αSMA, Abcam, Cambridge, UK), Collagen-1 (Abcam, Cambridge, UK), and Collagen-4 (BD/Pharmingen, San Diego, USA), and Alexa Fluor 488, 568 (Life Technologies, USA, Carlsbad, USA) secondary antibodies were used. Nuclear staining was performed using 4',6-diamidino-2-phenylindole (DAPI, Vector Labs, Burlingame, USA). Relative areas positive for αSMA and Collagen-1/4 per visual fields were analyzed at magnification ×40.

RNA Extraction, cDNA Synthesis and Real-Time PCR (qRT-PCR) Analysis

Animal tissues were shredded by TissueLyser LT (Qiagen, Hilden, Germany). Total RNA was extracted from the shredded tissues or cells by direct lysis with TRIzol reagent (Life Technologies, Carlsbad, USA) and RNA isolation was performed using the PureLink RNA Mini Kit according to the manufacturer's protocol. For first-strand cDNA synthesis, 1 µg of total RNA was prior treated with DNase I (Sigma-Aldrich, Munchen, Germany) and then converted into complementary DNA (cDNA) using the SuperScript II System (Life Technologies, Carlsbad, USA). For qRT-PCR analysis, 2 µl of diluted cDNA (1:10) as a template and the Fast SYBR Green Master Mix (Life Technologies, Carlsbad, USA) were used in a final volume of 20 µl for each reaction. Real-time PCR was performed in triplicate in a 96-well format by StepOne Plus realtime PCR system (Life Technologies, Carlsbad, USA). The relative expression levels were standardized to GAPDH using $2^{-\Delta\Delta Ct}$ methods.

Western Blot

Animal tissues were shredded by TissueLyser LT (Qiagen, Hilden, Germany). The shredded tissues and cells were lysed in NP40 buffer (Life Technologies, Carlsbad, USA) containing protease inhibitor cocktail (Roche, Mannheim, Germany). Lysates were mixed with loading buffer and heated at 95° C. for 5 min. Protein samples were resolved on 4-12% SDS-PAGE gels (Life Technologies, Carlsbad, USA) and transferred onto nitrocellulose membranes (GE Healthcare, Freiburg, Germany). Non-specific antibody binding was blocked with 5% nonfat milk in TBST buffer (50 mM Tris/150 mM NaCl/0.1% Tween-20) for 1 hour.

The membranes were incubated with primary antibodies in incubation solution (2% milk in TBST) overnight. Myc-tag antibody (Cell Signaling, Danvers, USA) was diluted 1:2500; Tubulin antibody (Sigma-Aldrich, Munchen, Germany) was diluted 1:5000; Rasal1 antibody (Abcam, Cambridge, UK) was diluted 1:1000. The membranes were washed 3 times with 2% milk in TBST. Then the membranes were incubated with HRP conjugated secondary antibody for 1 hour. Membranes were visualized using the LumiGLO chemiluminescence (Cell Signaling, Danvers, USA) and images were documented by a ChemiDoc MP System and processed using ImageLab software (Bio-Rad, Munchen, Germany).

Statistical Analysis

All qPCR data for RNA expression analysis (two or more biological replicates) were calculated using the ΔΔCT method. Student's t-test (GraphPad Prism 5.1) was used to obtain calculations of statistical significance. One-way Anova was used with Bonferroni adjustment for multiple parameter comparisons.

Results

Here we aimed to utilize both the high target specificity of sgRNA-guided Streptococcus pyogenes dCas9 and enzymatic effectiveness of TET3. We demonstrate specific targeting of one of the hypermethylated RASAL1, hypermethylated LRFN2 and hypermethylated KLOTHO through an all-in-one construct in which dCas9 is fused to the TET3 catalytic domain and which is specifically targeted to the RASAL1 promoter, the LRFN2 promoter and the KLOTHO promoter, respectively, by single-guide RNA (sgRNA). By expression of this Cas9-TET3CD-RASAL1-sgRNA we demonstrate successful re-expression of RASAL1 and attenuation of kidney fibrosis. The same is true for LRFN2 and KLOTHO as shown in the FIGS. 7 to 9.

Figure 1C:
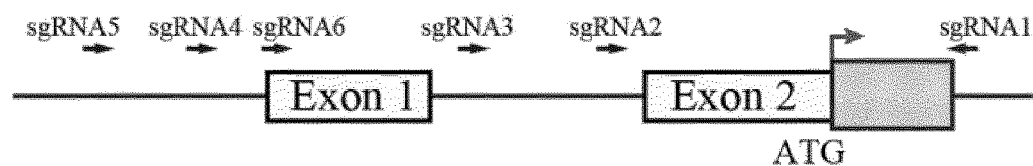

In order to generate a gene-specific hydroxymethylation system, we created a chimeric hydroxymethylase by fusing the TET3 catalytic domain (TET3CD) to the C-terminal domain of a double mutated Cas9 (dCas9), in which endonuclease catalytic residues D10A and H840A have been mutated to avoid cutting of DNA (FIG. 1*a, b*). To identify applicable short single-guide RNAs to enable specific targeting of the Cas9-TET3CD fusion protein to the RASAL1 promoter, we designed single guide RNAs (sgRNA), targeting different regions of the RASAL1 promoter. RASAL1-sgRNA1-3 target a proximal and RASAL1-sgRNA4 o 6 a distal region of the transcription start site (FIG. 1*c*). These sgRNAs as well as a LacZ control sgRNA were introduced into pLenti-dCas9 (pLenti-Cas9-RASAL1-sgRNA1-6) and pLenti-Cas9 (pLenti-Cas9-RASAL1-sgRNA1-6) vectors. While both pLenti-dCas9-RASAL1-sgRNA1-5 (harbouring mutated Cas9) and pLenti-Cas9-RASAL1-sgRNA1-6 (harbouring native Cas9) vectors displayed robust Cas9 or dCas9 expression respectively when transfected in HEK293, only pLenti-Cas9-RASAL1-sgRNA1-6 plasmids generated cleaved DNA fragments.

Figure 1D:
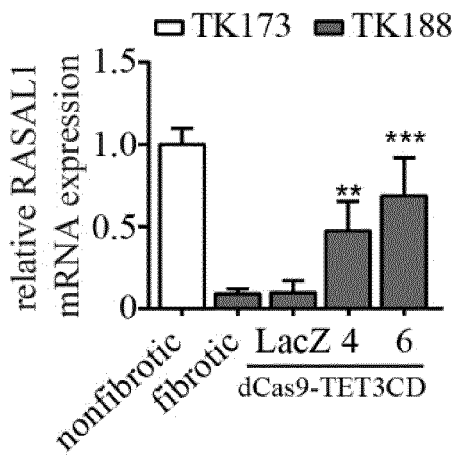

Upon establishing robust dCas9 expression of all five pLenti-dCas9-RASAL1-sgRNA1-6 vectors free of cleavage activity, we next introduced truncated TET3CD to generate specific human RASAL1 hydroxymethylation constructs (pLenti-dCas9-TET3CD-RASAL1-sgRNA1-5) and one control construct harbouring sgRNA targeted to LacZ coding sequence (pLenti-dCas9-TET3CD-LacZ-sgRNA). To test for RASAL1-hydroxymethylating activity we utilized TK188 fibrotic human renal fibroblasts with established robust RASAL1 CpG island promoter methylation. All five vectors induced robust expression of the dCas9-TET3CD fusion protein. The RASAL1 expression was significantly induced with the vectors containing the sgRNAs4 and 6 embodiment while less expression was observed with the negative control LacZ sgRNA and non-fibrotic TK173 cells (FIG. 1*d*). Since the highest level of RASAL1 re-expression was observed with the dCas9-TET3CD-RASAL1-sgRNA4, this vector was used for further experiments. It is speculated that the lower expression levels of the other vector constructs may be due to suboptimal positioning of the TET3CD or other conformational problems.

Figure 1E:
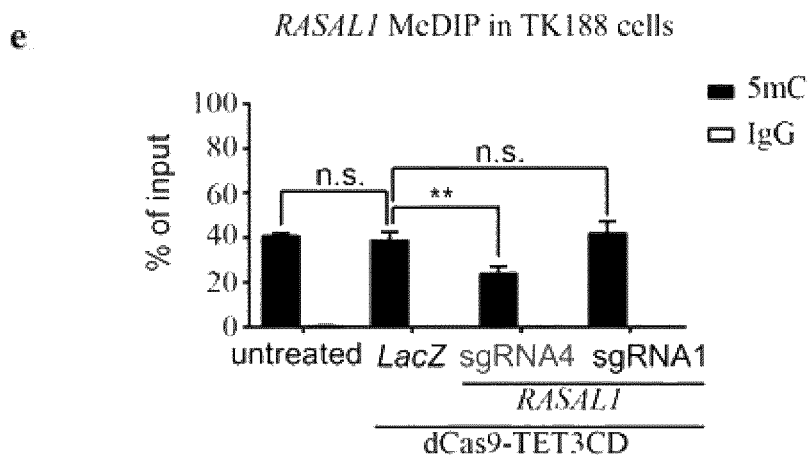

We hence performed hydroxymethylation- and methylation-specific hMeDIP and MeDIP assays for the dCas9-TET3CD fusion proteins guided by RASAL1-sgRNA4, RASAL1-sgRNA1, and LacZ-sgRNA revealing that among the different vectors, only dCas9-TET3CD-RASAL1-sgRNA4 induced significant RASAL1 promoter hydroxymethylation and reduced methylation (FIG. 1*e*). To determine if and which CpG sites could be demethylated in the RASAL1 promoter region after expression of dCas9-TET3CD-RASAL1-sgRNA4, bisulfite sequencing was performed. In contrast to dCas9-TET3CD-LacZ-sgRNA transduced cells, cells transduced to express dCas9-TET3CD-RASAL1-sgRNA4 demonstrated demethylation in the promoter region between −350 to +688, suggesting this to be a "critical promoter region". To gain single base-pair resolution for hydroxymethylation within the critical region, we performed glucosylation-mediated restriction enzyme sensitive PCR (gRES-PCR) revealing that upon treatment with T4-BGT and MspI the uncleaved RASAL1 PCR amplicon was only detectable in the cells transduced with dCas9-TET3CD-RASAL1-sgRNA4 but not in the other samples, confirming site-specific hydroxymethylation of RASAL1 promoter by this construct. Upon establishing that dCas9-TET3CD-RASAL1-sgRNA4 effectively induced RASAL1 CpG promoter hydroxymethylation and demethylation and subsequent rescue of RASAL1 expression, we identified all genes which were predicted to be targeted by sgRNA4 by the online program BlueHeron. A global methylation screen which was previously performed in fibrotic human renal fibroblasts revealed that among these 7 genes only RASAL1 was hypermethylated. We hence performed qRT-PCR for these genes, and no significant difference could be detected for any of the genes other than RASAL1 between cells transduced with dCas9-TET3CD-RASAL1-sgRNA4 and cells transduced with dCas9-TET3CD-LacZ-sgRNA. Similar results have been obtained with the LFRN2 and KLOTHO constructs described herein outlined in figures a and b as well as FIGS. 8*a* and *b*, respectively.

Figure 2A:
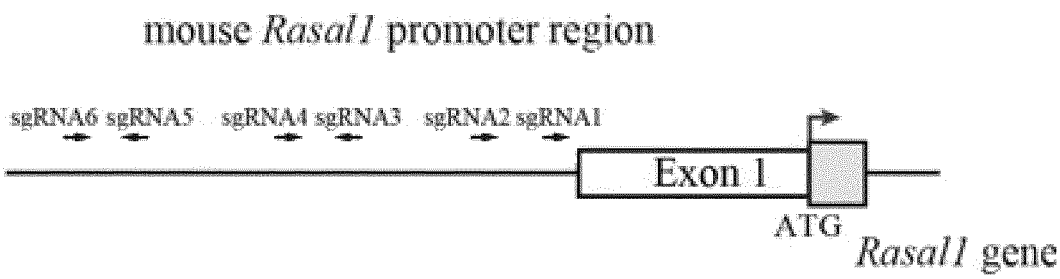
Figure 2B:
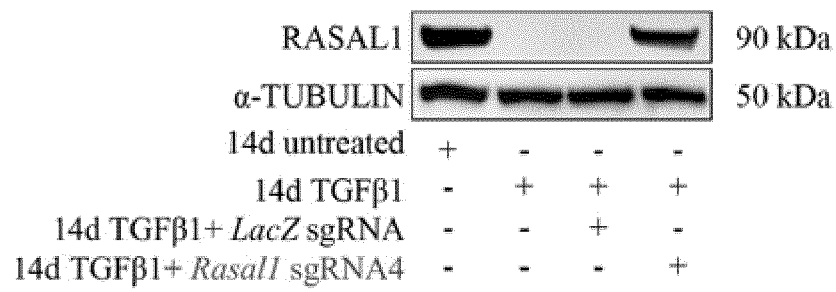
Figure 9A:
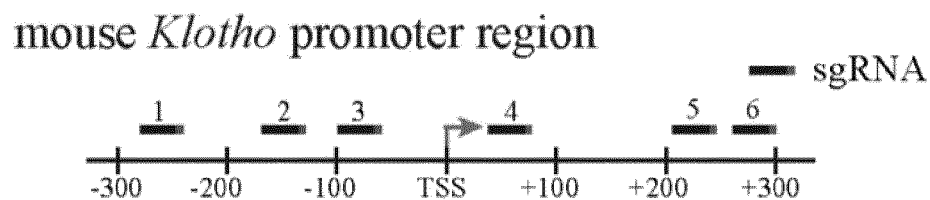
Figure 9B:
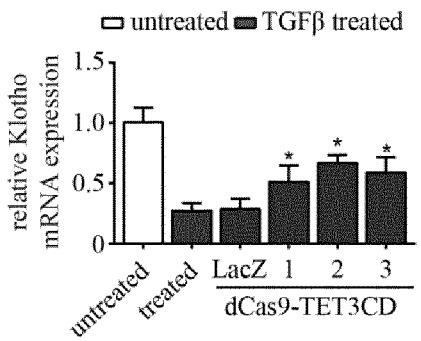

To assure our demethylation strategy is also functional in different cells and species, we decided to validate our system in primary mouse kidney fibroblasts (mKFs) in which RASAL1 expression is reduced via promoter methylation by prolonged exposure to TGFβ1, whereas hydroxymethylation level is low and unchanged by TGFβ1. We designed 6 different sgRNAs spreading over the whole RASAL1 promoter region (FIG. 2*a*) and introduced them into a pLenti-dCas9-TET3CD vector as described above (pLenti-dCas9-TET3CD-RASAL1-sgRNA1-6) to transduce mKFs 10 days after TGFβ1 treatment. Upon confirming robust dCas9 expression devoid of unspecific cleavage activity, we identified that two of the vectors (dCas9-TET3CD-RASAL1-sgRNA4 and 6) rescued significantly RASAL1 expression (FIG. 2*b*) and that rescued RASAL1 expression corresponded with enhanced RASAL1 promoter hydroxymethylation and attenuated promoter methylation. Bisulfite sequencing identified −375 to −87 as the critical region within the murine RASAL1 promoter. qRT-PCR analysis of predicted sgRNA4 target genes did not reveal any unspecific gene activation. Similar results are obtained with the mouse KLOTHO gene as shown in FIGS. 9*a* and 9*b*.

In summary, we demonstrate successful targeted hydroxymethylation and demethylation of aberrantly methylated RASAL1 through lentiviral delivery of a construct encoding a fusion protein of Cas9 devoid of cleavage activity and the catalytic domain of TET3, which is targeted to the RASAL1 promoter CpG through specific single guide RNA.

Figure 3A:
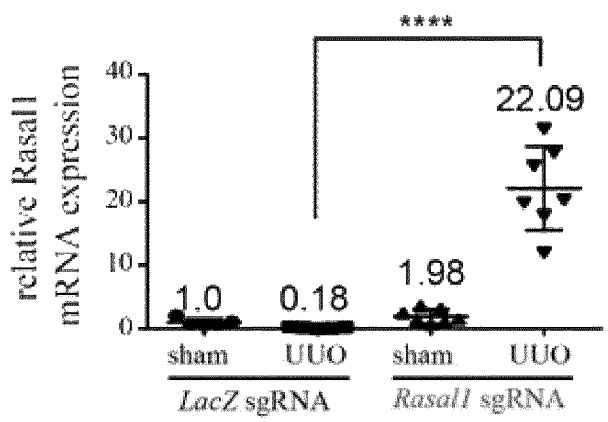
Figure 3B:
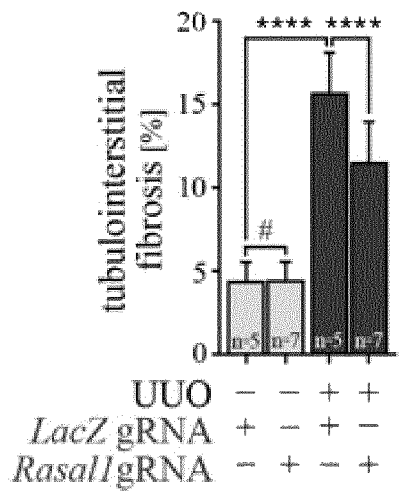
Figure 5:
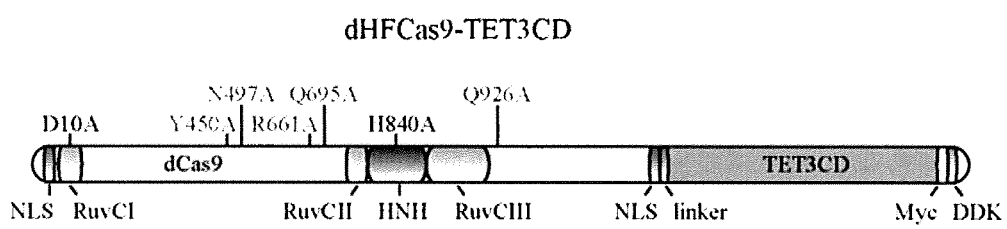
Figure 6A:
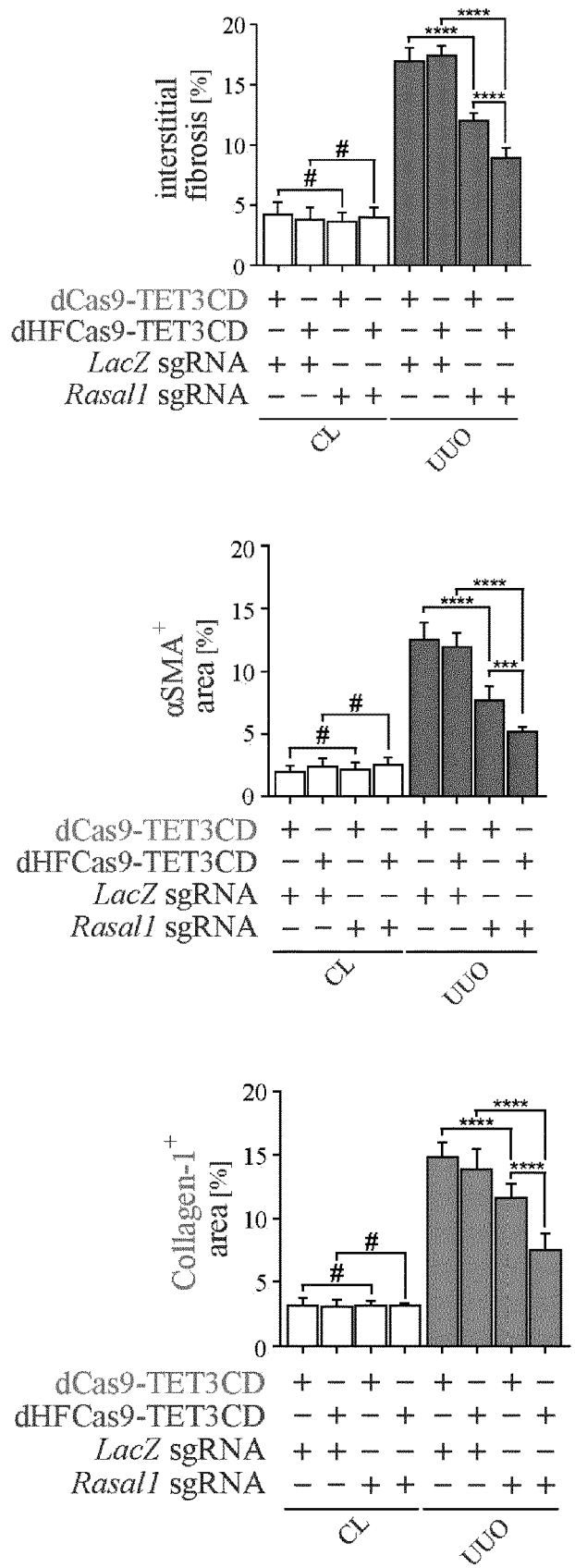

To test the efficacy of the established dCas9-TET3CD-RASAL1 system as well as the similar KLOTHO system in vivo, we utilized the mouse model of unilateral ureteral obstruction (UUO), which displays robust RASAL1 promoter methylation within interstitial fibroblasts and KLOTHO methylation in tubular epithelial cells, and in which transcriptional RASAL1 and KLOTHO suppression contributes causally to fibroblast accumulation and disease progression (Bechtel, W. et al. *Nat Med* 16, 544-550 (2010), Tampe, B. et al. *Journal of the American Society of Nephrology* 25, 905-912 (2014)). Based on previous studies which demonstrated effective lentiviral transduction of kidney cells upon vector delivery through renal arteries, we injected lentivirus harbouring either dCas9-TET3CD-RASAL1-sgRNA or dCas9-TET3CD-LacZ-sgRNA into the renal artery of UUO-challenged kidneys. The expression of the dCas9-TET3CD protein was detected by a DDK-tag antibody within interstitial fibroblasts in both UUO and the contralateral (CL) kidneys upon injection of either dCas9-TET3CD-RASAL1-sgRNA or dCas9-TET3CD-LacZ-sgRNA. Rescue of RASAL1 expression was observed exclusively in mice which received dCas9-TET3CD-RASAL1-sgRNA, but not in mice injected with the dCas9-TET3CD-LacZ-sgRNA control vector (FIG. 3*a*), and increased RASAL1 mRNA expression correlated with increased RASAL1 hydroxymethylation and reduced methylation. Fibrosis was significantly attenuated in dCas9-TET3CD-RASAL1-sgRNA treated mice, but not in mice administered with the dCas9-TET3CD-LacZ-sgRNA control vector (FIG. 3*b*). Attenuated fibrosis in dCas9-TET3CD-RASAL1-sgRNA treated mice correlated with blunted accumulation of fibroblasts and of type I Collagen, correlating with RASAL1 hydroxymethylation, demethylation and rescued RASAL1 expression. Our study is in line with previous reports which demonstrated that demethylation and rescue of RASAL1 expression attenuate fibrosis and fibroblast accumulation in the UUO model Tampe, B. et al. *E Bio Medicine* 2, 19-36 (2015). Further, renal fibrosis, accumulation of fibroblasts and of type I collagen were significantly attenuated in dCas9/dHFCas9-TET3CD-Rasal1-sgRNA4 treated mice, but not in mice administered with the dCas9/dHFCas9-TET3CD-LacZ-sgRNA control vectors (FIG. 6*a*). Interestingly, even though Rasal1 hydroxymethylation and restoration of Rasal1 expression was equally effective, attenuation of kidney fibrosis was almost 50% and thereby more effective in dHF—as compared to less than 30% in dCas9-TET3CD-Rasal1-sgRNA treated mice (FIG. 6*a*), which is likely due to the reduction of off-target effects in the dHFCas9-TET3CD as compared to the dCas9-TET3CD system (FIG. 6*a*). A scheme of the dhfCas9-Tet3CD is shown in FIG. 5.

Figure 6B:
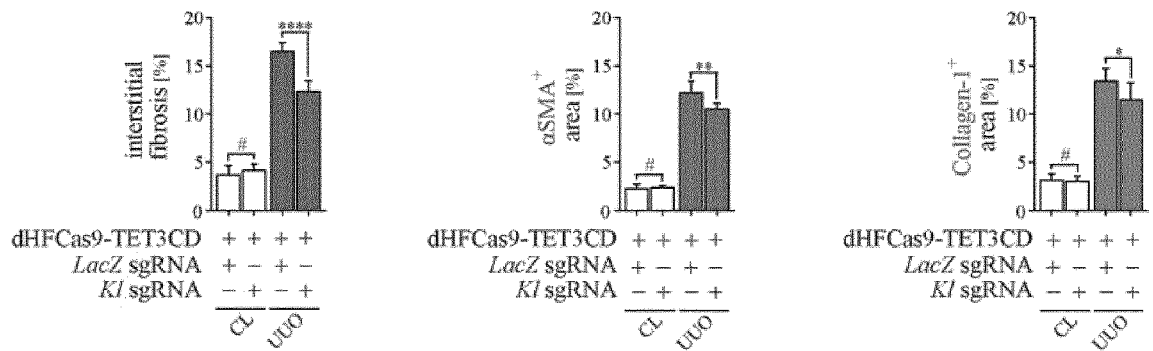

After establishing that dHFCas9-TET3CD is superior to the dCas9-TET3CD system, we continued to use the dHFCas9-TET3CD system for targeted hydroxymethylation of Klotho in tubular epithelial cells in order to test its anti-fibrotic potential in vivo. To target methylated Klotho in tubular epithelial cells, we performed retrograde injection of dHFCas9-TET3CD-Klotho-sgRNA and dHFCas9-TET3CD-LacZ-sgRNA control viruses into the ureters of UUO-challenged and of contralateral control kidneys and analyzed the kidneys after 10 days. Similar as with Rasal1, Klotho expression was successfully restored to approximately 50% of the physiological level by dHFCas9-TET3CD-Klothos-gRNA but not with LacZ-sgRNA and restoration correlated with reduced Klotho promoter methylation levels (FIG. 6*b*). Kidney fibrosis was significantly reduced by 25.4% by dHFCas9-Klotho-sgRNA as compared to dHF-TET3CD-LacZ-sgRNA injection (FIG. 6*b*), and this reduction in fibrosis correlated with blunted accumulation of fibroblasts and of type I Collagen (FIG. 6*b*), correlating with Klotho demethylation and rescued Klotho expression.

Here we provide proof-of-principle that by using a novel dCas9/dHFCas9-TET3CD all-in-one fusion protein approach, single methylated genes can be specifically targeted and transcriptionally re-activated in vitro as well as in vivo in a disease model. Based on the example of three different genes (RASAL1, LRFN2, and KLOTHO) which are known to be hypermethylated in specific cell types or upon stimulation with TGFβ1, we demonstrate that targeted TET3-mediated hydroxymethylation is a feasible, reliable and fast technology which results in demethylation and transcriptional re-activation of these genes. Because we also demonstrate that use of the mutated wild-type SpCas9 in this technology results in substantial off-target effects we developed a new high-fidelity Cas9-based approach which reduced off-target genes by 85%. The relevance of reduction of off-target genes was proven by testing our gene-specific demethylation technologies in a disease model in vivo, which to our knowledge has not been done before.

Among the three genes for which we established gene-specific hydroxymethylation vectors, we selected Rasal1 and Klotho for in vivo studies, as both genes have been well studied in context of kidney fibrosis in both human and mouse models: Klotho has been shown to be hypermethylated and transcriptionally silenced in kidney fibrosis patients and in corresponding mouse models, and lack of Klotho is causally linked to kidney fibrosis in mice. Rasal1 has been shown to be transcriptionally silenced and hypermethylated in both human and mouse kidney fibrosis. Because the causality between Rasal1 and kidney fibrosis had not yet been addressed, we generated Rasal1 knockout mice in which Rasal1 expression was reduced by 70%. In these mice, kidney fibrosis was substantially increased upon challenge with UUO, thus causally linking lack of Rasal1 with kidney fibrosis.

Predominant expression of Rasal1 occurs in kidney fibroblasts and of Klotho in tubular epithelial cells. Both cell types are separated by a basal membrane. Because it has been shown that lentiviral constructs do not cross basal membranes, we established different routes of lentiviral delivery to primarily target interstitial cells (via parenchymal injection) or epithelial cells (via the ureter). By these respective modes of injection we were able to specifically re-activate Klotho expression in tubular epithelial cells by dHFCas9-TET3CD-Klotho-sgRNA and Rasal1 expression in interstitial cells by dCas9/dHFCas9-TET3CD-Rasal1-sgRNA constructs in the UUO mouse model of kidney fibrosis and to ameliorate kidney fibrosis. Interestingly, the therapeutic anti-fibrotic effect of dCas9-TET3CD-Rasal1-sgRNA construct was much smaller (less than 30% fibrosis reduction) as compared to the dHFCas9-TET3CD-Rasal1-sgRNA (almost 50% reduction in total interstitial fibrosis) despite a complete re-activation of Rasal1 expression by both constructs. It appears likely that this is due to off-target effects of dCas9-TET3CD which re-activated pro-fibrotic genes Anxa4, and Nlrp5 (off-targeted by dCas9-TET3CD but not by dHFCas9-TET3CD) along with Rasal1, highlighting the need for the use of high-fidelity Cas9 in this context.

By fusing mutated CRISPR/Cas9 with the Tet3 catalytic domain, we achieved superior specificity and reached a more extended region of demethylation from the target site as compared to previous Zinc finger and TALE-based approaches. Our study is in line with previous reports which demonstrated gene-specific reactivation of epigenetically silenced genes within cultured cells using dCas9-p300, dCas-LSD1, dCas9-VP64 and dCas9-TET1CD fusion constructs in vitro (Hilton, I. B. et al. *Nature biotechnology* 33, 510-517 (2015); Choudhury, S. R., Cui, Y., Lubecka, K., Stefanska, B. & Irudayaraj, J. *Oncotarget* (2016); Xu, X. et al. *Cell discovery* 2, 16009 (2016)). Unlike our approach those studies did not use an all-in-one fusion protein but two individual components, which are only functional when both are delivered and expressed simultaneously in the same cell, thus limiting their utility in vivo. Our study is further in line with a very recent report, where a demethylating system based on dCas9 fused to the repeating peptide GCN4, which recruits an anti-GCN4 single-chain variable fragment (scFv) fused to the effector domain of TET1 CD was utilized Morita, S. et al. *Nature biotechnology* (2016) doi:10.1038/nbt.3658. This system was successfully introduced into embryonic mouse brain by in utero electroporation and thereby reactivated expression of specific genes including Gfap in vivo. Unlike this study, which reached effective demethylation of CpG sites 100 bp from the target sites, we reach an even longer range of >180 bp from the target sites. This may be due to the fact that (unlike all these previous studies which used TET1CD) we use TET3CD, which is a substantially larger domain than TET1CD. Furthermore, our application by lentiviral delivery is made possible through a considerably smaller size of construct exempt from negligible elements in our study as compared to constructs utilized in that study and thus presents a more feasible therapeutic approach in vivo as compared to electroporation-based gene delivery. Thus, although there are previous reports with respect to gene-specific demethylation both in vitro and in vivo, to our knowledge, this study is the first to describe an effective CRISPR-based epigenetic therapy in a disease model.

FIGURE LEGENDS

FIG. 1. dCas9-TET3CD fusion protein induces targeted RASAL1 promoter demethylation in human cells.

(a) Architecture of dCas9 (D10A/H840A)-TET3CD (TET3 catalytic domain) fusion protein in complex with sgRNA and its target promoter region to induce hydroxymethylation. (b) Schematic of domain structure of the dCas9-TET3CD fusion protein. The dCas9 with positions of the RuvCI, RuvCII, RuvCII- and HNH-domains are indicated. The mutated amino acids D10A and H840A are located at RuvCI and HNH domains, respectively. A nuclear localization signal (NLS) was added to both N- and C-terminal. The catalytic domain of Ten-eleven translocation gene 3 (TET3) was engineered to the C-terminal of dCas9. Myc and DDK epitope tags were added to the C-terminal. (c) Location and direction (5' to 3') of sgRNA targeting sites (black arrows) within the human RASAL1 locus. (d) Human fibrotic TK188 cells (with known RASAL1 hypermethylation) were transduced with lentivirus expressing demethylation constructs guided by RASAL1-sgRNAs or by LacZ control sgRNA. RASAL1 mRNA expression was significantly up-regulated only in cells transduced with dCas9-TET3CD-RASAL1-sgRNA 4 and 6. TK173 are used as non-fibrotic control cells. Results were normalized to reference gene GAPDH (expression is presented as mean value; error bars represent S.D.; n=3; *, p<0.001). (e) TK188 cells transduced with dCas9-TET3CD-RASAL1 show significantly reduced RASAL1 promoter methylation by MeDIP-qPCR assay (e). The results were calculated relative to the input. The data is presented as mean value; error bars represent S.D.; n=3 independent transductions; n.s., not significant; , p<0.01; ***, p<0.001.

FIG. 2. dCas9-TET3CD fusion protein induces targeted RASAL1 promoter demethylation in mouse cells.

(a) Schematic of mouse Rasal1 locus. Black arrows indicate the location and direction (5' to 3') of sgRNA targeting sites. (b) Western blots showing restored RASAL1 protein expression in mKFs which were transduced with the demethylation construct guided by sgRNA4 after TGFβ1 treatment. The membrane was restriped and re-probed with α-TUBULIN antibody to serve as equal loading control.

FIG. 3. dCas9-TET3CD fusion protein ameliorates kidney fibrosis in an experimental model of kidney fibrotic (a) qRT-PCR results showing that Rasal1 mRNA expression was significantly induced in UUO kidney samples transduced with dCas9-TET3CD-Rasal1-sgRNA4 but not in samples transduced with control dCas9-TET3CD-LacZ-sgRNA. Results were normalized to reference gene Gapdh (expression is presented as mean value; error bars represent S.E.M.; n=5 in LacZ sgRNA group and n=7 in Rasal1 sgRNA group; **, p<0.0001). (b) Quantification of immunostained positive cells in each group (data is presented as mean value; error bars represent S.E.M.; HPF, high-power field; n=5 in LacZ sgRNA group and n=7 in Rasal1 sgRNA group; **, p<0.0001).

Figure 4:
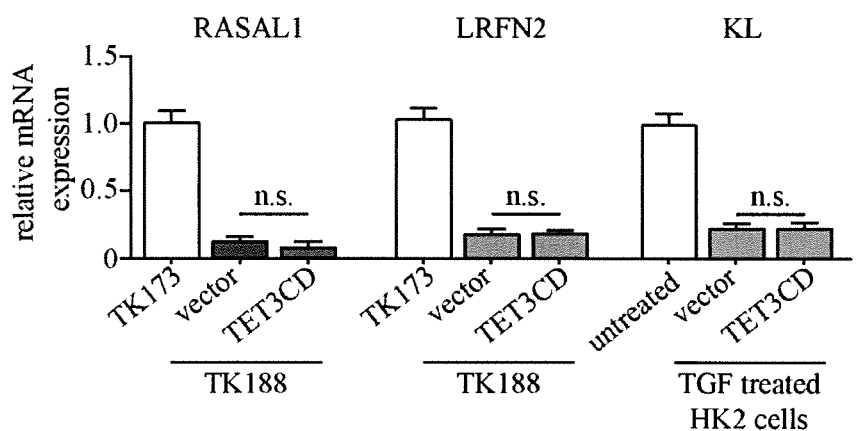

FIG. 4 Overexpression of TET3 catalytic domain does not restore the expression of 3 different aberrantly methylated genes. qRT-PCR results showing that only overexpression of TET3 catalytic domain alone does not induce the expression of 3 different aberrantly methylated genes RASAL1, LRFN2 in TK188 fibrotic human kidney fibroblasts and does not induce the expression of KL in TGFβ1-treated HK2 cells. Results were normalized to reference gene GAPDH (expression is presented as mean value; error bars represent S.E.M.; n=3 independent biological replicates).

FIG. 5: Schematic of domain structure of the dHFCas9-TET3CD fusion protein. 5 additional mutated amino acids Y450A, N497A, R661A, Q695A, and Q926A are marked.

FIG. 6: (a) Quantification of the percentage of total interstitial fibrosis and immunostained positive cells in each group is depicted (data is presented as mean value; error bars represent S.E.M.; n≥5 in each group; #, not significant; *, p<0.001; **, p<0.0001). Both dCas9-TET3CD-Rasal1-sgRNA and dHFCas9-TET3CD-Rasal1-sgRNA lentivirus transduced UUO-operated kidneys show significantly decreased interstitial fibrosis level and a significantly decreased number of α-SMA- and Collagen-1-positive cells. where dHFCas9-TET3CD shows significantly better efficacies when compared to dCas9-TET3CD.

(b) Quantification of the percentage of total interstitial fibrosis and immunostained positive cells in each group are depicted (data is presented as mean value; error bars represent S.E.M.; n≥5 in each group; #, not significant; *, p<0.05; , p<0.01; **, p<0.0001). UUO-challenged kidneys transduced with lentivirus expressing dHFCas9-TET3CD-Kl-sgRNA show significantly decreased interstitial fibrosis level and a significantly decreased number of α-SMA- and Collagen-1-positive cells.

Figure 7A:
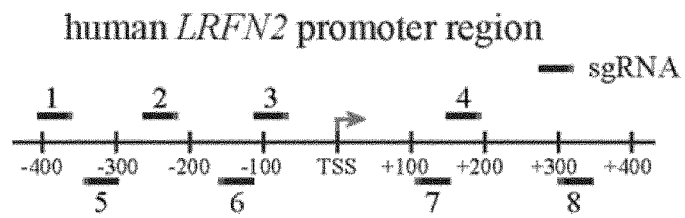
Figure 7B:
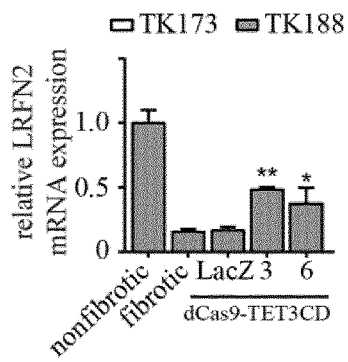
Figure 8A:
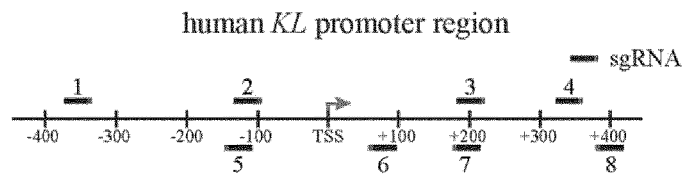

FIG. 7. dCas9-TET3CD fusion protein induces targeted LRFN2 promoter demethylation in human cells.

(a) Schematic of human LRFN2 locus. Black arrows indicate the location and direction (5' to 3') of sgRNA targeting sites.

(b) Human fibrotic TK188 cells were transduced with lentivirus expressing demethylation constructs guided by LRFN2-sgRNAs1-8 or by LacZ control sgRNA. LRFN2 mRNA expression was significantly up-regulated only in cells transduced with dCas9-TET3CD-LRFN2-sgRNA3/6. Results were normalized to reference gene GAPDH (expression is presented as mean value; error bars represent S.D.; n=3; ***, p<0.001).

Figure 8B:
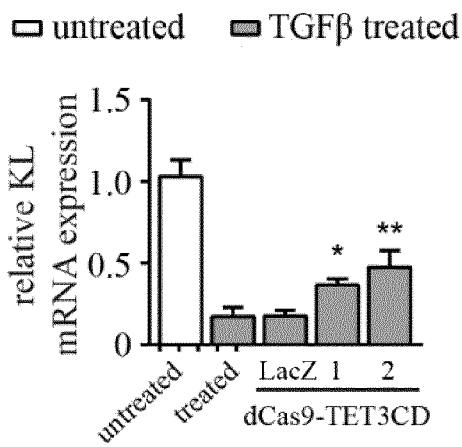

FIG. 8. dCas9-TET3CD fusion protein induces targeted human KLOTHO promoter demethylation in human cells.

(a) Schematic of human KLOTHO locus. Black arrows indicate the location and direction (5' to 3') of sgRNA targeting sites.

(b) TGFβ1-treated human tubular epithelial cells were transduced with lentivirus expressing demethylation constructs guided by KLOTHO-sgRNAs1-8 or by LacZ control sgRNA. KLOTHO mRNA expression was significantly up-regulated only in cells transduced with dCas9-TET3CD-KLOTHO-sgRNA1/2. Results were normalized to reference gene GAPDH (expression is presented as mean value; error bars represent S.D.; n=3; ***, p<0.001).

FIG. 9. dCas9-TET3CD fusion protein induces targeted mouse Klotho promoter demethylation in mouse cells.

(a) Schematic of mouse Klotho locus. Black arrows indicate the location and direction (5' to 3') of sgRNA targeting sites.

(b) TGFβ1-treated mouse tubular epithelial cells were transduced with lentivirus expressing demethylation constructs guided by Klotho-sgRNAs1-6 or by LacZ control sgRNA. Klotho mRNA expression was significantly up-regulated only in cells transduced with dCas9-TET3CD-Klotho-sgRNA1-3. Results were normalized to reference gene Gapdh (expression is presented as mean value; error bars represent S.D.; n=3; ***, p<0.001).

The invention claimed is:

1. A method for the treatment of a disease, disorder or condition selected from fibrosis, neuronal degeneration or cancer comprising the steps of re-expression of hypermethylated RASAL1 in cells, comprising the steps of:
introducing in cells i) nucleic acid encoding a fusion protein composed of an inactive CRISPR system and a DNA dioxygenase in this order and ii) gRNA, said gRNA guiding said fusion protein composed of an inactive CRISPR based system and a DNA dioxygenase to RASAL1; and
demethylation of hypermethylated RASAL1 for re-expression of RASAL1 in said cells.

2. The method according to claim 1 wherein said fibrosis, neuronal degeneration or cancer is selected from the group consisting of kidney fibrosis, liver fibrosis, heart fibrosis, lung fibrosis, breast cancer, hodgkin lymphoma, adenocarcinoma, colon cancer, thyroid cancer, liver cancer, gastric cancer, and colorectal cancer.

3. The method according to claim 1 wherein the DNA dioxygenase is selected from TET protein family.

4. The method according to claim 1 wherein the hypermethylated region of the RASAL1 gene is the promoter region and the gRNA is a gRNA guiding the fusion protein composed of the inactive CRISPR based system and the DNA dioxygenase to the promoter region of RASAL1.

5. The method according to claim 1 wherein the inactive CRISPR system is a mutated Cas9 system and/or a mutated Cpf system.

6. The method according to claim 1 wherein the hypermethylated RASAL1 gene region is the promoter region of the RASAL1 gene, the inactivated CRISPR system is the inactive dCas9 having the mutations D10A and H840A and the DNA dioxygenase is the TET3 catalytic domain (TET3CD) or the TET1 catalytic domain (TET1CD).

7. The method of claim 1 wherein the DNA dioxygenase to RASAL1 gene is to the promoter region of the RASAL1 gene.

8. An in vitro method for re-expression of hypermethylated RASAL1 in cells comprising the steps of:
introducing in cells nucleic acid encoding a gRNA guiding a fusion protein composed of an inactive CRISPR based system and a DNA dioxygenase to RASAL1 gene, and nucleic acid encoding a fusion protein composed of an inactive CRISPR system and a DNA dioxygenase in this order;
demethylation of hypermethylated RASAL1 for re-expression of RASAL1 in said cells.

9. The method according to claim 8 wherein the DNA dioxygenase is selected from TET protein family.

10. The method according to claim 8 wherein the hypermethylated region of the RASAL1 gene is the promoter region and the gRNA is a gRNA guiding the fusion protein composed of the inactive CRISPR based system and the DNA dioxygenase to the promoter region of RASAL1.

11. The method according to claim 8 wherein the inactive CRISPR system is a mutated Cas9 system and/or a mutated Cpf system.

12. The method according to claim 8 wherein the hypermethylated RASAL1 gene region is the promoter region of the RASAL1 gene, the inactivated CRISPR system is the inactive dCas9 or dHFCas9 having the mutations D10A and H840A and the DNA dioxygenase is the TET3 catalytic domain (TET3CD) or the TET1 catalytic domain (TET1CD).

13. The method of claim 8 wherein the DNA dioxygenase to RASAL1 gene is to the promoter region of the RASAL1 gene.

* * * * *

SEQUENCE LISTING

<160> NUMBER OF SEQ ID NOS: 23

<210> SEQ ID NO 1
<211> LENGTH: 1800
<212> TYPE: DNA
<213> ORGANISM: homo sapiens

<400> SEQUENCE: 1

```
caggagaggt gacgcgtggc ccacgcctca aaggacaaca atcagaatat caaacacttt      60
ctggacgtgt attaggtact tgtcactgtc ctgagacttt tatcttcatt aactctttta     120
attctttcaa aatcctgtga ctgaaatgca atgtcatcct cactcaacag atgagaaaac     180
caaaccaaag cacagagagg ttgaatggct tacccaagtc cagacagcta ccaaatggca     240
gagccaggat tcgaacccct ggaaggcaaa tcagttactg actgtgagac ctctgccaag     300
ttatttaatc cctctgaacc tcagtttctt tatccataaa ctgcggataa tggggtaaca     360
gtggagtagt gtgtagtgca catctggaga caaaaatgag ctaatcccag taaagcgctt     420
agaacagtgc ctggcaccca tgaagtgttc aaacaactgt agatgacttt ttatcatcgc     480
tgtagtggtt atcttcaagc cttcccctcc cccatctggc cgcggcttcc tccccgcag     540 tgccagcccg tgacgttaga gcagagtctg ggttctgtgt ttaactggaa actagaacga     600
gatggaaggg gatgttcaag gcccctccct tgactctgaa cggaccccca gggaacatgc     660
gaccctctct ctggcgacgc ctcccaccca ccactaatac ttgctcctgg accgggggc      720 gcggaggttg gagagaggag gcaggtgtct gcatggtagg caaggagggg tggggcgga     780 gaggtgtgaa tatgttggat gagggacagg cggggcaca gaccatgtct tttaagccca      840
atgccaactc accaggagcc agcggccacg cccatcagga cggggcccc tccccacctg      900 gcggtgcacc cttgtctccg ccgcccgtgc gctctggcgc gcatgactgg ggtgccggta     960
gagggcgcgc gaggggggccc ggggtcaggt gggggacccc attggaggcg ggattgtggg    1020
gaggtccctg ggccgccct cccgcccct gcccgccag cctgcttgtc tggagctcca      1080
gacgcctcgg caagagcccg ctgcgccccc tgcgcgctcc tcctgctcgg agcacggctc    1140
ctacctgtag agtccggacg ggcgctccct ccccgggcac ctacaccttc tcctctttcg    1200
gaaatctccc atccagctac ccgggtctcg gacaggcggc actgggacca cgaggcaggg    1260
agccaggctt gaagcaggtg acatgtagac gtccctggt ccagcctcgg aacctgagcg    1320
cccttctgcc tggaaagttt gtggctaggc gccatggcca agagcagctc cctgaatgtt    1380
```

| | |
|---|---|
| cgcgtggtgg agggccgcgc gctgcctgcc aaggacgtgt gagtactcct cgggcgcttc | 1440 |
| tgggtgaggg gcgcgcaagg cctggggtgg ggccgacgtc gcccttccg cgtgccaggg | 1500 |
| cgggttggca ggagggcgag gggttcttgt ccaagactgg tcttgggca gttccgcttt | 1560 |
| aaaggggcga gaggccgcat gcccatggct gtcccggtgg gagggggcg cctagagtta | 1620 |
| gcagatgccc cgcctcaccc ccgggcaggg gaggggtgt ctttgttccc gggatgtact | 1680 |
| aaaggggtc gtccagagct gaagagggga ttagagggcc atattctgtc agatctggga | 1740 |
| ggggagaaag cggggggtct cttccttagt ccaggcagat gttggaggtg gctcctccag | 1800 |

<210> SEQ ID NO 2
<211> LENGTH: 2070
<212> TYPE: DNA
<213> ORGANISM: Mus musculus

<400> SEQUENCE: 2

| | |
|---|---|
| cagcctttct gaatactccc cagttagtta aaccacagac ttcgagaagg aaggtagctc | 60 |
| tgccagcgtc taccctggga caagccttct gttcacatga tcccatttaa aactcgcaaa | 120 |
| ggcacaaagc atcttgggaa cggaggaaaa aggaagaaga ctttgcgtg ggggtgtgg | 180 |
| aagggcctcc taaaagcctt gccaggagac gtgacattta aggcacacct tgaagaagaa | 240 |
| gaacaacaaa aaataccgta tgctctgtgc ctgattaggt gtgtaccact cttctgaggc | 300 |
| ccgtgtggga gtatctcatt taattctctc tcaaccctgt aaatgagaca cgtgtcgtgt | 360 |
| catgctccct gaacagatga gaaaactaaa ccgaggaaca gagaggttaa gtgactgact | 420 |
| catctaagac caggcattac cacatctacc aaatggcagc agagtcagaa ctcaaaccca | 480 |
| gaaaggagac ttctggcaag tgtcccccac ctctcaggac cccaatttgt gtgtgtgtgt | 540 |
| ttattttggt ttttgttttt gttttgtttt taaatccata gatagagggc tcccatgaca | 600 |
| tacagagttg ccgagggctc aaaactgaga taatccccat gaaaggctca agccgtgcct | 660 |
| ggaacttggt taagtgttcg aggattgcag atggctctta tcgtgccgcc cgggcggtgt | 720 |
| tatctccgcg cctcccctcc ccctgcggcc gcggcttcct ccccccgcagt ggcagccggt | 780 |
| gacgtgggag cctccgctgg cacactccgg gtttaattgg agacgaagag aagatgcaag | 840 |
| gggatgttcg aggtccctcc ctccactcgc atcagacccc cagggagcgt gcgccgcctg | 900 |
| ccgcccagag agagtactgt tccgggaccc cgaggctggt gttggggtgg caggtggagg | 960 |
| aggtgggaga ggtgtggagg tgctgggttg agggccggca ggagacaccc gggttcttgg | 1020 |
| agggttcaaa ataagctcag taacagcctg cagccctgct tgactgctcg cgcctcctcc | 1080 |
| acccccacccc ttgacccata gcgcctgggg ggtccccggc tgagtgcagt agcctggggt | 1140 |
| gccagcaggg ggcgctcgcg tagggggttca gggcgggcgg ggcagctgcg gggggcggga | 1200 |
| tcgggaggga cctcccgggc ggcagacgcc tggctcagcc tgcccagatc gcagcgcaca | 1260 |
| gctacctgta gctctggacg catgtcccct tccgggaccc agcacgcctc cctcctagcc | 1320 |
| ctgcatccag cccactcgca ccccagaccc ggacacgtgg gaaccggctg acagcgtgct | 1380 |
| tggcccgcag ctgatgacat gtagggtcac ctcctggtcc agcctcagaa cctcggcaga | 1440 |
| ctccttgcct ggaaagtttg ggactgtgcg acatggccaa gagcggctcg ctgagtatcc | 1500 |
| gcgtggtgga gggacgagca ctgcccgcca aggacgtgtg agtccccggg tgcccactgg | 1560 |
| ggtgcgtaga agggttgtgg ggagccctgt ttaggacccg ctgctgggga tccgccctcc | 1620 |
| ctattctgtg ggagggggcg cccaggctta gcaggtgcgg caccttgctc cctccacctc | 1680 |

-continued

```
caccccaccc ccgggaagga gggtgtcttt gttctaggat gtccccaagt gggtcttaca    1740
ggacgggtta aaggagctct ggactgggta ctcttagagc ctaggagggg gttgagcgat    1800
cccttcctta gctccagcag gtgttggagg tggggcttct ccgagcgaca aagaggcta     1860 tccagagacc actaggggta gagcccctga gggctgtgat ccagactgac cccaagattt    1920
ttcatgcctt aggggtggtg tttagatttg cagcgcttca ccaggtggtc ctctaacccg    1980 gaacccggt tttgtacctg caaacctagg gtggactatc tcagatctcc aagtgatcta     2040
agagacactc gcaggtgcac gtgtgatagg                                      2070
```

```
<210> SEQ ID NO 3
<211> LENGTH: 20
<212> TYPE: DNA
<213> ORGANISM: artificial
<220> FEATURE:
<223> OTHER INFORMATION: probe

<400> SEQUENCE: 3
agtactcaca cgtccttggc                                                  20

<210> SEQ ID NO 4
<211> LENGTH: 20
<212> TYPE: DNA
<213> ORGANISM: artificial
<220> FEATURE:
<223> OTHER INFORMATION: probe

<400> SEQUENCE: 4
ggcgcgcatg actggggtgc                                                  20

<210> SEQ ID NO 5
<211> LENGTH: 20
<212> TYPE: DNA
<213> ORGANISM: artificial
<220> FEATURE:
<223> OTHER INFORMATION: probe

<400> SEQUENCE: 5
aagcccaatg ccaactcacc                                                  20

<210> SEQ ID NO 6
<211> LENGTH: 20
<212> TYPE: DNA
<213> ORGANISM: artificial
<220> FEATURE:
<223> OTHER INFORMATION: probe

<400> SEQUENCE: 6
atccataaac tgcggataat                                                  20

<210> SEQ ID NO 7
<211> LENGTH: 20
<212> TYPE: DNA
<213> ORGANISM: artificial
<220> FEATURE:
<223> OTHER INFORMATION: probe

<400> SEQUENCE: 7
atttggtagc tgtctggact                                                  20

<210> SEQ ID NO 8
<211> LENGTH: 20
<212> TYPE: DNA
<213> ORGANISM: artificial
```

```
<220> FEATURE:
<223> OTHER INFORMATION: probe

<400> SEQUENCE: 8
accccttgac ccatagcgcc                                               20

<210> SEQ ID NO 9
<211> LENGTH: 20
<212> TYPE: DNA
<213> ORGANISM: artificial
<220> FEATURE:
<223> OTHER INFORMATION: probe

<400> SEQUENCE: 9
gagacacccg ggttcttgga                                               20

<210> SEQ ID NO 10
<211> LENGTH: 20
<212> TYPE: DNA
<213> ORGANISM: artificial
<220> FEATURE:
<223> OTHER INFORMATION: probe

<400> SEQUENCE: 10
cgaacactta accaagttcc                                               20

<210> SEQ ID NO 11
<211> LENGTH: 20
<212> TYPE: DNA
<213> ORGANISM: artificial
<220> FEATURE:
<223> OTHER INFORMATION: probe

<400> SEQUENCE: 11
catgacatac agagttgccg                                               20

<210> SEQ ID NO 12
<211> LENGTH: 20
<212> TYPE: DNA
<213> ORGANISM: artificial
<220> FEATURE:
<223> OTHER INFORMATION: probe

<400> SEQUENCE: 12
taaatgagat actcccacac                                               20

<210> SEQ ID NO 13
<211> LENGTH: 20
<212> TYPE: DNA
<213> ORGANISM: artificial
<220> FEATURE:
<223> OTHER INFORMATION: probe

<400> SEQUENCE: 13
aaggaagaag agctttgcgt                                               20

<210> SEQ ID NO 14
<211> LENGTH: 5
<212> TYPE: PRT
<213> ORGANISM: artificial
<220> FEATURE:
<223> OTHER INFORMATION: peptide

<400> SEQUENCE: 14

Gly Gly Gly Ser Gly
1               5
```

<210> SEQ ID NO 15
<211> LENGTH: 2376
<212> TYPE: PRT
<213> ORGANISM: artificial
<220> FEATURE:
<223> OTHER INFORMATION: peptide

<400> SEQUENCE: 15

Met Ala Pro Lys Lys Arg Lys Val Gly Arg Gly Met Asp Lys Lys
1               5                   10                  15

Tyr Ser Ile Gly Leu Ala Ile Gly Thr Asn Ser Val Gly Trp Ala Val
                20                  25                  30

Ile Thr Asp Glu Tyr Lys Val Pro Ser Lys Lys Phe Lys Val Leu Gly
                35                  40                  45

Asn Thr Asp Arg His Ser Ile Lys Lys Asn Leu Ile Gly Ala Leu Leu
            50                  55                  60

Phe Asp Ser Gly Glu Thr Ala Glu Ala Thr Arg Leu Lys Arg Thr Ala
65                  70                  75                  80

Arg Arg Arg Tyr Thr Arg Arg Lys Asn Arg Ile Cys Tyr Leu Gln Glu
                85                  90                  95

Ile Phe Ser Asn Glu Met Ala Lys Val Asp Asp Ser Phe Phe His Arg
                100                 105                 110

Leu Glu Glu Ser Phe Leu Val Glu Glu Asp Lys Lys His Glu Arg His
            115                 120                 125

Pro Ile Phe Gly Asn Ile Val Asp Glu Val Ala Tyr His Glu Lys Tyr
        130                 135                 140

Pro Thr Ile Tyr His Leu Arg Lys Lys Leu Val Asp Ser Thr Asp Lys
145                 150                 155                 160

Ala Asp Leu Arg Leu Ile Tyr Leu Ala Leu Ala His Met Ile Lys Phe
                165                 170                 175

Arg Gly His Phe Leu Ile Glu Gly Asp Leu Asn Pro Asp Asn Ser Asp
            180                 185                 190

Val Asp Lys Leu Phe Ile Gln Leu Val Gln Thr Tyr Asn Gln Leu Phe
        195                 200                 205

Glu Glu Asn Pro Ile Asn Ala Ser Gly Val Asp Ala Lys Ala Ile Leu
    210                 215                 220

Ser Ala Arg Leu Ser Lys Ser Arg Arg Leu Glu Asn Leu Ile Ala Gln
225                 230                 235                 240

Leu Pro Gly Glu Lys Lys Asn Gly Leu Phe Gly Asn Leu Ile Ala Leu
                245                 250                 255

Ser Leu Gly Leu Thr Pro Asn Phe Lys Ser Asn Phe Asp Leu Ala Glu
            260                 265                 270

Asp Ala Lys Leu Gln Leu Ser Lys Asp Thr Tyr Asp Asp Asp Leu Asp
        275                 280                 285

Asn Leu Leu Ala Gln Ile Gly Asp Gln Tyr Ala Asp Leu Phe Leu Ala
    290                 295                 300

Ala Lys Asn Leu Ser Asp Ala Ile Leu Leu Ser Asp Ile Leu Arg Val
305                 310                 315                 320

Asn Thr Glu Ile Thr Lys Ala Pro Leu Ser Ala Ser Met Ile Lys Arg
                325                 330                 335

Tyr Asp Glu His His Gln Asp Leu Thr Leu Leu Lys Ala Leu Val Arg
            340                 345                 350

Gln Gln Leu Pro Glu Lys Tyr Lys Glu Ile Phe Phe Asp Gln Ser Lys
        355                 360                 365

```
Asn Gly Tyr Ala Gly Tyr Ile Asp Gly Gly Ala Ser Gln Glu Glu Phe
    370             375                 380

Tyr Lys Phe Ile Lys Pro Ile Leu Glu Lys Met Asp Gly Thr Glu Glu
385             390                 395                 400

Leu Leu Val Lys Leu Asn Arg Glu Asp Leu Arg Lys Gln Arg Thr
            405                 410                 415

Phe Asp Asn Gly Ser Ile Pro His Gln Ile His Leu Gly Glu Leu His
            420                 425                 430

Ala Ile Leu Arg Arg Gln Glu Asp Phe Tyr Pro Phe Leu Lys Asp Asn
        435                 440                 445

Arg Glu Lys Ile Glu Lys Ile Leu Thr Phe Arg Ile Pro Tyr Tyr Val
    450                 455                 460

Gly Pro Leu Ala Arg Gly Asn Ser Arg Phe Ala Trp Met Thr Arg Lys
465             470                 475                 480

Ser Glu Glu Thr Ile Thr Pro Trp Asn Phe Glu Glu Val Val Asp Lys
            485                 490                 495

Gly Ala Ser Ala Gln Ser Phe Ile Glu Arg Met Thr Asn Phe Asp Lys
            500                 505                 510

Asn Leu Pro Asn Glu Lys Val Leu Pro Lys His Ser Leu Leu Tyr Glu
        515                 520                 525

Tyr Phe Thr Val Tyr Asn Glu Leu Thr Lys Val Lys Tyr Val Thr Glu
    530                 535                 540

Gly Met Arg Lys Pro Ala Phe Leu Ser Gly Glu Gln Lys Lys Ala Ile
545             550                 555                 560

Val Asp Leu Leu Phe Lys Thr Asn Arg Lys Val Thr Val Lys Gln Leu
            565                 570                 575

Lys Glu Asp Tyr Phe Lys Lys Ile Glu Cys Phe Asp Ser Val Glu Ile
            580                 585                 590

Ser Gly Val Glu Asp Arg Phe Asn Ala Ser Leu Gly Thr Tyr His Asp
        595                 600                 605

Leu Leu Lys Ile Ile Lys Asp Lys Asp Phe Leu Asp Asn Glu Glu Asn
        610                 615                 620

Glu Asp Ile Leu Glu Asp Ile Val Leu Thr Leu Thr Leu Phe Glu Asp
625             630                 635                 640

Arg Glu Met Ile Glu Glu Arg Leu Lys Thr Tyr Ala His Leu Phe Asp
            645                 650                 655

Asp Lys Val Met Lys Gln Leu Lys Arg Arg Arg Tyr Thr Gly Trp Gly
        660                 665                 670

Arg Leu Ser Arg Lys Leu Ile Asn Gly Ile Arg Asp Lys Gln Ser Gly
        675                 680                 685

Lys Thr Ile Leu Asp Phe Leu Lys Ser Asp Gly Phe Ala Asn Arg Asn
    690                 695                 700

Phe Met Gln Leu Ile His Asp Asp Ser Leu Thr Phe Lys Glu Asp Ile
705             710                 715                 720

Gln Lys Ala Gln Val Ser Gly Gln Gly Asp Ser Leu His Glu His Ile
            725                 730                 735

Ala Asn Leu Ala Gly Ser Pro Ala Ile Lys Lys Gly Ile Leu Gln Thr
            740                 745                 750

Val Lys Val Val Asp Glu Leu Val Lys Val Met Gly Arg His Lys Pro
        755                 760                 765

Glu Asn Ile Val Ile Glu Met Ala Arg Glu Asn Gln Thr Thr Gln Lys
    770                 775                 780
```

```
Gly Gln Lys Asn Ser Arg Glu Arg Met Lys Arg Ile Glu Glu Gly Ile
785                 790                 795                 800

Lys Glu Leu Gly Ser Gln Ile Leu Lys Glu His Pro Val Glu Asn Thr
            805                 810                 815

Gln Leu Gln Asn Glu Lys Leu Tyr Leu Tyr Tyr Leu Gln Asn Gly Arg
        820                 825                 830

Asp Met Tyr Val Asp Gln Glu Leu Asp Ile Asn Arg Leu Ser Asp Tyr
            835                 840                 845

Asp Val Asp Ala Ile Val Pro Gln Ser Phe Leu Lys Asp Asp Ser Ile
850                 855                 860

Asp Asn Lys Val Leu Thr Arg Ser Asp Lys Asn Arg Gly Lys Ser Asp
865                 870                 875                 880

Asn Val Pro Ser Glu Glu Val Val Lys Lys Met Lys Asn Tyr Trp Arg
            885                 890                 895

Gln Leu Leu Asn Ala Lys Leu Ile Thr Gln Arg Lys Phe Asp Asn Leu
        900                 905                 910

Thr Lys Ala Glu Arg Gly Gly Leu Ser Glu Leu Asp Lys Ala Gly Phe
    915                 920                 925

Ile Lys Arg Gln Leu Val Glu Thr Arg Gln Ile Thr Lys His Val Ala
    930                 935                 940

Gln Ile Leu Asp Ser Arg Met Asn Thr Lys Tyr Asp Glu Asn Asp Lys
945                 950                 955                 960

Leu Ile Arg Glu Val Lys Val Ile Thr Leu Lys Ser Lys Leu Val Ser
                965                 970                 975

Asp Phe Arg Lys Asp Phe Gln Phe Tyr Lys Val Arg Glu Ile Asn Asn
            980                 985                 990

Tyr His His Ala His Asp Ala Tyr Leu Asn Ala Val Val Gly Thr Ala
        995                 1000                1005

Leu Ile Lys Lys Tyr Pro Lys Leu Glu Ser Glu Phe Val Tyr Gly
    1010                1015                1020

Asp Tyr Lys Val Tyr Asp Val Arg Lys Met Ile Ala Lys Ser Glu
    1025                1030                1035

Gln Glu Ile Gly Lys Ala Thr Ala Lys Tyr Phe Phe Tyr Ser Asn
    1040                1045                1050

Ile Met Asn Phe Phe Lys Thr Glu Ile Thr Leu Ala Asn Gly Glu
    1055                1060                1065

Ile Arg Lys Arg Pro Leu Ile Glu Thr Asn Gly Glu Thr Gly Glu
    1070                1075                1080

Ile Val Trp Asp Lys Gly Arg Asp Phe Ala Thr Val Arg Lys Val
    1085                1090                1095

Leu Ser Met Pro Gln Val Asn Ile Val Lys Lys Thr Glu Val Gln
    1100                1105                1110

Thr Gly Gly Phe Ser Lys Glu Ser Ile Leu Pro Lys Arg Asn Ser
    1115                1120                1125

Asp Lys Leu Ile Ala Arg Lys Lys Asp Trp Asp Pro Lys Lys Tyr
    1130                1135                1140

Gly Gly Phe Asp Ser Pro Thr Val Ala Tyr Ser Val Leu Val Val
    1145                1150                1155

Ala Lys Val Glu Lys Gly Lys Ser Lys Lys Leu Lys Ser Val Lys
    1160                1165                1170

Glu Leu Leu Gly Ile Thr Ile Met Glu Arg Ser Ser Phe Glu Lys
    1175                1180                1185

Asn Pro Ile Asp Phe Leu Glu Ala Lys Gly Tyr Lys Glu Val Lys
```

```
                1190              1195              1200
Lys Asp Leu Ile Ile Lys Leu Pro Lys Tyr Ser Leu Phe Glu Leu
    1205              1210              1215

Glu Asn Gly Arg Lys Arg Met Leu Ala Ser Ala Gly Glu Leu Gln
    1220              1225              1230

Lys Gly Asn Glu Leu Ala Leu Pro Ser Lys Tyr Val Asn Phe Leu
    1235              1240              1245

Tyr Leu Ala Ser His Tyr Glu Lys Leu Lys Gly Ser Pro Glu Asp
    1250              1255              1260

Asn Glu Gln Lys Gln Leu Phe Val Glu Gln His Lys His Tyr Leu
    1265              1270              1275

Asp Glu Ile Ile Glu Gln Ile Ser Glu Phe Ser Lys Arg Val Ile
    1280              1285              1290

Leu Ala Asp Ala Asn Leu Asp Lys Val Leu Ser Ala Tyr Asn Lys
    1295              1300              1305

His Arg Asp Lys Pro Ile Arg Glu Gln Ala Glu Asn Ile Ile His
    1310              1315              1320

Leu Phe Thr Leu Thr Asn Leu Gly Ala Pro Ala Ala Phe Lys Tyr
    1325              1330              1335

Phe Asp Thr Thr Ile Asp Arg Lys Arg Tyr Thr Ser Thr Lys Glu
    1340              1345              1350

Val Leu Asp Ala Thr Leu Ile His Gln Ser Ile Thr Gly Leu Tyr
    1355              1360              1365

Glu Thr Arg Ile Asp Leu Ser Gln Leu Gly Gly Asp Pro Lys Lys
    1370              1375              1380

Lys Arg Lys Val Ser Arg Gly Gly Ser Gly Tyr Tyr Thr His
    1385              1390              1395

Leu Gly Ser Gly Pro Thr Val Ala Ser Ile Arg Glu Leu Met Glu
    1400              1405              1410

Glu Arg Tyr Gly Glu Lys Gly Lys Ala Ile Arg Ile Glu Lys Val
    1415              1420              1425

Ile Tyr Thr Gly Lys Glu Gly Lys Ser Ser Arg Gly Cys Pro Ile
    1430              1435              1440

Ala Lys Trp Val Ile Arg Arg His Thr Leu Glu Glu Lys Leu Leu
    1445              1450              1455

Cys Leu Val Arg His Arg Ala Gly His His Cys Gln Asn Ala Val
    1460              1465              1470

Ile Val Ile Leu Ile Leu Ala Trp Glu Gly Ile Pro Arg Ser Leu
    1475              1480              1485

Gly Asp Thr Leu Tyr Gln Glu Leu Thr Asp Thr Leu Arg Lys Tyr
    1490              1495              1500

Gly Asn Pro Thr Ser Arg Arg Cys Gly Leu Asn Asp Asp Arg Thr
    1505              1510              1515

Cys Ala Cys Gln Gly Lys Asp Pro Asn Thr Cys Gly Ala Ser Phe
    1520              1525              1530

Ser Phe Gly Cys Ser Trp Ser Met Tyr Phe Asn Gly Cys Lys Tyr
    1535              1540              1545

Ala Arg Ser Lys Thr Pro Arg Lys Phe Arg Leu Ala Gly Asp Asn
    1550              1555              1560

Pro Lys Glu Glu Glu Val Leu Arg Lys Ser Phe Gln Asp Leu Ala
    1565              1570              1575

Thr Glu Val Ala Pro Leu Tyr Lys Arg Leu Ala Pro Gln Ala Tyr
    1580              1585              1590
```

-continued

```
Gln Asn Gln Val Thr Asn Glu Ile Ala Ile Asp Cys Arg Leu
1595                1600                1605

Gly Leu Lys Glu Gly Arg Pro Phe Ala Gly Val Thr Ala Cys Met
1610                1615                1620

Asp Phe Cys Ala His Ala His Lys Asp Gln His Asn Leu Tyr Asn
    1625                1630                1635

Gly Cys Thr Val Val Cys Thr Leu Thr Lys Glu Asp Asn Arg Cys
1640                1645                1650

Val Gly Lys Ile Pro Glu Asp Glu Gln Leu His Val Leu Pro Leu
1655                1660                1665

Tyr Lys Met Ala Asn Thr Asp Glu Phe Gly Ser Glu Glu Asn Gln
1670                1675                1680

Asn Ala Lys Val Gly Ser Gly Ala Ile Gln Val Leu Thr Ala Phe
1685                1690                1695

Pro Arg Glu Val Arg Arg Leu Pro Glu Pro Ala Lys Ser Cys Arg
1700                1705                1710

Gln Arg Gln Leu Glu Ala Arg Lys Ala Ala Ala Glu Lys Lys Lys
1715                1720                1725

Ile Gln Lys Glu Lys Leu Ser Thr Pro Glu Lys Ile Lys Gln Glu
1730                1735                1740

Ala Leu Glu Leu Ala Gly Ile Thr Ser Asp Pro Gly Leu Ser Leu
1745                1750                1755

Lys Gly Gly Leu Ser Gln Gln Gly Leu Lys Pro Ser Leu Lys Val
1760                1765                1770

Glu Pro Gln Asn His Phe Ser Ser Phe Lys Tyr Ser Gly Asn Ala
1775                1780                1785

Val Val Glu Ser Tyr Ser Val Leu Gly Asn Cys Arg Pro Ser Asp
1790                1795                1800

Pro Tyr Ser Met Asn Ser Val Tyr Ser Tyr His Ser Tyr Tyr Ala
1805                1810                1815

Gln Pro Ser Leu Thr Ser Val Asn Gly Phe His Ser Lys Tyr Ala
1820                1825                1830

Leu Pro Ser Phe Ser Tyr Tyr Gly Phe Pro Ser Ser Asn Pro Val
1835                1840                1845

Phe Pro Ser Gln Phe Leu Gly Pro Gly Ala Trp Gly His Ser Gly
1850                1855                1860

Ser Ser Gly Ser Phe Glu Lys Lys Pro Asp Leu His Ala Leu His
1865                1870                1875

Asn Ser Leu Ser Pro Ala Tyr Gly Gly Ala Glu Phe Ala Glu Leu
1880                1885                1890

Pro Ser Gln Ala Val Pro Thr Asp Ala His His Pro Thr Pro His
1895                1900                1905

His Gln Gln Pro Ala Tyr Pro Gly Pro Lys Glu Tyr Leu Leu Pro
1910                1915                1920

Lys Ala Pro Leu Leu His Ser Val Ser Arg Asp Pro Ser Pro Phe
1925                1930                1935

Ala Gln Ser Ser Asn Cys Tyr Asn Arg Ser Ile Lys Gln Glu Pro
1940                1945                1950

Val Asp Pro Leu Thr Gln Ala Glu Pro Val Pro Arg Asp Ala Gly
1955                1960                1965

Lys Met Gly Lys Thr Pro Leu Ser Glu Val Ser Gln Asn Gly Gly
1970                1975                1980
```

```
Pro Ser His Leu Trp Gly Gln Tyr Ser Gly Gly Pro Ser Met Ser
    1985                1990                1995

Pro Lys Arg Thr Asn Gly Val Gly Gly Ser Trp Gly Val Phe Ser
    2000                2005                2010

Ser Gly Glu Ser Pro Ala Ile Val Pro Asp Lys Leu Ser Ser Phe
    2015                2020                2025

Gly Ala Ser Cys Leu Ala Pro Ser His Phe Thr Asp Gly Gln Trp
    2030                2035                2040

Gly Leu Phe Pro Gly Glu Gly Gln Gln Ala Ala Ser His Ser Gly
    2045                2050                2055

Gly Arg Leu Arg Gly Lys Pro Trp Ser Pro Cys Lys Phe Gly Asn
    2060                2065                2070

Ser Thr Ser Ala Leu Ala Gly Pro Ser Leu Thr Glu Lys Pro Trp
    2075                2080                2085

Ala Leu Gly Ala Gly Asp Phe Asn Ser Ala Leu Lys Gly Ser Pro
    2090                2095                2100

Gly Phe Gln Asp Lys Leu Trp Asn Pro Met Lys Gly Glu Glu Gly
    2105                2110                2115

Arg Ile Pro Ala Ala Gly Ala Ser Gln Leu Asp Arg Ala Trp Gln
    2120                2125                2130

Ser Phe Gly Leu Pro Leu Gly Ser Ser Glu Lys Leu Phe Gly Ala
    2135                2140                2145

Leu Lys Ser Glu Glu Lys Leu Trp Asp Pro Phe Ser Leu Glu Glu
    2150                2155                2160

Gly Pro Ala Glu Glu Pro Pro Ser Lys Gly Ala Val Lys Glu Glu
    2165                2170                2175

Lys Gly Gly Gly Gly Ala Glu Glu Glu Glu Glu Leu Trp Ser
    2180                2185                2190

Asp Ser Glu His Asn Phe Leu Asp Glu Asn Ile Gly Gly Val Ala
    2195                2200                2205

Val Ala Pro Ala His Gly Ser Ile Leu Ile Glu Cys Ala Arg Arg
    2210                2215                2220

Glu Leu His Ala Thr Thr Pro Leu Lys Lys Pro Asn Arg Cys His
    2225                2230                2235

Pro Thr Arg Ile Ser Leu Val Phe Tyr Gln His Lys Asn Leu Asn
    2240                2245                2250

Gln Pro Asn His Gly Leu Ala Leu Trp Glu Ala Lys Met Lys Gln
    2255                2260                2265

Leu Ala Glu Arg Ala Arg Ala Arg Gln Glu Glu Ala Ala Arg Leu
    2270                2275                2280

Gly Leu Gly Gln Gln Glu Ala Lys Leu Tyr Gly Lys Lys Arg Lys
    2285                2290                2295

Trp Gly Gly Thr Val Val Ala Glu Pro Gln Gln Lys Glu Lys Lys
    2300                2305                2310

Gly Val Val Pro Thr Arg Gln Ala Leu Ala Val Pro Thr Asp Ser
    2315                2320                2325

Ala Val Thr Val Ser Ser Tyr Ala Tyr Thr Lys Val Thr Gly Pro
    2330                2335                2340

Tyr Ser Arg Trp Ile Thr Arg Pro Leu Glu Gln Lys Leu Ile Ser
    2345                2350                2355

Glu Glu Asp Leu Ala Ala Asn Asp Ile Leu Asp Tyr Lys Asp Asp
    2360                2365                2370

Asp Asp Lys
```

2375

<210> SEQ ID NO 16
<211> LENGTH: 20
<212> TYPE: DNA
<213> ORGANISM: artificial
<220> FEATURE:
<223> OTHER INFORMATION: probe

<400> SEQUENCE: 16 acttttatc atcgctgtag                    20

<210> SEQ ID NO 17
<211> LENGTH: 20
<212> TYPE: DNA
<213> ORGANISM: artificial
<220> FEATURE:
<223> OTHER INFORMATION: probe

<400> SEQUENCE: 17
cgcccgactc cctcccagat                    20

<210> SEQ ID NO 18
<211> LENGTH: 20
<212> TYPE: DNA
<213> ORGANISM: artificial
<220> FEATURE:
<223> OTHER INFORMATION: probe

<400> SEQUENCE: 18
gccagaggcg cccaggaacc                    20

<210> SEQ ID NO 19
<211> LENGTH: 20
<212> TYPE: DNA
<213> ORGANISM: artificial
<220> FEATURE:
<223> OTHER INFORMATION: probe

<400> SEQUENCE: 19
ctccccgacg aagccgctcc                    20

<210> SEQ ID NO 20
<211> LENGTH: 20
<212> TYPE: DNA
<213> ORGANISM: artificial
<220> FEATURE:
<223> OTHER INFORMATION: probe

<400> SEQUENCE: 20
tcgcaggtaa ttattgccag                    20

<210> SEQ ID NO 21
<211> LENGTH: 20
<212> TYPE: DNA
<213> ORGANISM: artificial
<220> FEATURE:
<223> OTHER INFORMATION: probe

<400> SEQUENCE: 21
ctccctgagc tggctgcagc                    20

<210> SEQ ID NO 22
<211> LENGTH: 20
<212> TYPE: DNA
<213> ORGANISM: artificial

```
<220> FEATURE:
<223> OTHER INFORMATION: probe

<400> SEQUENCE: 22
tgtgctctct ctgggcaccc                                               20

<210> SEQ ID NO 23
<211> LENGTH: 20
<212> TYPE: DNA
<213> ORGANISM: artificial
<220> FEATURE:
<223> OTHER INFORMATION: probe

<400> SEQUENCE: 23
cccccgtgcc aggccggagt                                               20
```